(12) United States Patent
Harding et al.

(10) Patent No.: US 8,709,782 B2
(45) Date of Patent: Apr. 29, 2014

(54) TARGETED GENE DELETIONS FOR POLYSACCHARIDE SLIME FORMERS

(75) Inventors: Nancy E. Harding, San Diego, CA (US); Yamini N. Patel, San Diego, CA (US); Russell J. Coleman, San Diego, CA (US)

(73) Assignee: C.P. Kelco U.S., Inc., Atlanta, GA (US)

( * ) Notice: Subject to any disclaimer, the term of this patent is extended or adjusted under 35 U.S.C. 154(b) by 95 days.

(21) Appl. No.: 12/983,935

(22) Filed: Jan. 4, 2011

(65) Prior Publication Data
US 2011/0281334 A1 Nov. 17, 2011

Related U.S. Application Data

(62) Division of application No. 11/347,341, filed on Feb. 3, 2006, now Pat. No. 7,888,333.

(60) Provisional application No. 60/649,559, filed on Feb. 4, 2005.

(51) Int. Cl.
| | | |
|---|---|---|
| *C12N 1/20* | (2006.01) | |
| *C12P 19/04* | (2006.01) | |
| *C12Q 1/68* | (2006.01) | |
| *C12N 15/74* | (2006.01) | |
| *C07H 21/04* | (2006.01) | |

(52) U.S. Cl.
USPC ......... 435/252.3; 435/6.1; 435/101; 435/471; 536/23.2

(58) Field of Classification Search
None
See application file for complete search history.

(56) References Cited

U.S. PATENT DOCUMENTS

| 5,854,034 A | 12/1998 | Pollock et al. |
| 6,605,461 B2 | 8/2003 | Yamazaki et al. |
| 6,620,775 B2 | 9/2003 | Winston et al. |
| 2003/0100078 A1 | 5/2003 | Harding et al. |

FOREIGN PATENT DOCUMENTS

WO WO-0164897 A2 * 9/2001

OTHER PUBLICATIONS

Harding et al., "Organization of genes required for gellan polysaccharide biosynthesis in *Sphingomonas elodea* ATCC 31461," Journal of Industrial Microbiology & Biotechnology, Feb. 2004, pp. 70-82, vol. 31, No. 2, Springer Berlin, Germany.

Yamazaki et al., "Linkage of genes essential for synthesis of a polysaccharide capsule in *Sphingomonas* Strain S88," Journal of Bacteriology, May 1996, pp. 2676-2687, vol. 178, No. 9, American Society for Microbiology, Washington, DC.

SA-Correia et al., "Extracellular Polysaccharides Review: Gellan gum biosynthesis in *Sphingomonas paucimobilis* ATCC 31461: Genes, enzymes and exopolysaccharide production engineering," Journal of Industrial Microbiology & Biotechnology, Oct. 2002, pp. 170-176, vol. 29, No. 4, Springer Berllin, Germany.

Seo et al., "Isolation of an exopolysaccharide-producing Bacterium, *Sphingomonas* sp. CS101, which forms an unusual type of Sphingan," Bioscience, Biotechnology, and Biochemistry, 2004, pp. 1146-1148, vol. 68, No. 5, Japan Society for Bioscience, Biotechnology, and Agrochemistry, Tokyo, Japan.

West, 2002, "Isolation of a Mutant Strain of *Pseudomonas* sp. ATCC 31461 Exhibiting Elevated Polysaccharide Production," Journal of Industrial Microbiology & Biotechnology, 29:185-188.

* cited by examiner

*Primary Examiner* — Iqbal H Chowdhury
(74) *Attorney, Agent, or Firm* — Sutherland Asbill & Brennan LLP

(57) ABSTRACT

The present invention provides improved polysaccharides (e.g., gellan and diutan) produced by mutant gene M or gene N *Sphingomonas* strains containing at least one genetic modification that favors slime-forming polysaccharide production. Methods of making the mutant *Sphingomonas* strains and the culture broth containing such mutant *Sphingomonas* strains are also provided.

11 Claims, 6 Drawing Sheets

Slime forming characteristics of S60WTC::Δ*gelM-gelN*

Slime forming characteristics of S60WTC *gelN* and *gelI* Mutants

Figure 4

ATG TTC AAC CGG CGT GAC TCT AGA CTC GGT CAC CAG GTC TGA
 ↓            ↓       ↓                            ↓
Start DpsN   Stop DpsM  XbaI                   Stop DpsN Met Phe Asn Arg Arg Asp Ser Arg Leu Gly His Gln Val *

Slime forming characteristics of *dps*M mutants

A

B

TARGETED GENE DELETIONS FOR POLYSACCHARIDE SLIME FORMERS

CROSS REFERENCES TO RELATED APPLICATIONS

This is a divisional application of U.S. application Ser. No. 11/347,341 filed Feb. 3, 2006 now U.S. Pat. No. 7,888,333, allowed, which claims the benefit of U.S. Provisional Application No. 60/649,559, filed Feb. 4, 2005. The prior applications are incorporated herein by reference in their entirety.

FIELD OF THE INVENTION

This invention is related to the area of sphingan polysaccharide production. In particular, it relates to site-directed genetic methods for improving sphingan-producing strains.

BACKGROUND OF THE INVENTION

*Sphingomonas* strains, such as ATCC 53159 and ATCC 31461, produce copious amounts of capsular polysaccharide. While under some conditions polysaccharide may be released from the cell [5, 6], during growth with abundant carbon source as in fermentation, the polysaccharide is firmly attached to the cell surface. Attempts to increase productivity of fermentations for diutan and gellan may be limited by the capsular nature of the polysaccharide, which may impair uptake of nutrients. Also, if there are a limited number of sites for biosynthesis of the polysaccharide, there may be a maximum amount of polysaccharide that can be produced by each cell. The polysaccharide gellan has been observed to be involved in cell clumping since mutants that do not make any polysaccharide grow uniformly in suspension [3]. These cell clumps may interfere with techniques such as determination of cell number by optical density, centrifugation of cells, e.g., for isolation of DNA or protein, and separation or lysis of cells for polysaccharide purification.

The mechanism of attachment and the genes involved in attachment of polysaccharide to the cell surface in *Sphingomonas* have not been previously determined. Induced mutants of *Sphingomonas* strains ATCC 31461, ATCC 31555, ATCC 31554, and ATCC 21423 that produce polysaccharide in a slime form have been isolated, but the genes mutated were not determined, and the methods of inducing and selecting the mutants were not disclosed [10]. Genes for biosynthesis of gellan [3, 8], diutan [1] and sphingan S-88 [9] have been isolated. The functions of many of these genes were assigned by biochemical tests or by homology to genes of known functions in databases such as GenBank. For example, genes have been identified that are involved in assembly of the tetrasaccharide repeat unit [7, 8], and in synthesis of the precursor dTDP-L-rhamnose [3, 9]. It would be expected that genes affecting only attachment of polysaccharide to the cell surface would still have the polysaccharide producing phenotype (i.e., mucoid colonies on solid media and viscous broth).

A cluster of 18 genes for gellan biosynthesis spanning 21 kb was described, in addition to four genes for gellan synthesis not in the cluster [3]. The DNA sequences were deposited in GenBank in June 2003 (Accession number AY217008). Among the genes in the cluster were gelM, gelN, and gelI. A deletion of most of adjacent genes gelM and gelN was constructed. The gelI gene was inactivated by an insertion. The gelM-gelN deletion strain and the gelI mutant were shown to produce somewhat reduced amounts of gellan and more fluid broths, and the gellan produced was shown to have the same composition as gellan from the wild-type strain. The attachment of the polysaccharide to the cell was not reported The *Sphingomonas elodea* gelR, gelS, and gelG genes appear to be in an operon in the same order as in the S-88 sps gene cluster, but not adjacent to the genes in the cluster of 18 genes [3]. The GelR protein was somewhat smaller than its S-88 homolog (659 vs. 670 amino acids) with 49% identity, and had homology to surface layer proteins and other membrane proteins. The DNA sequences of gelR, gelS and gelG genes were deposited in GenBank in June 2003 (Accession number AY220099). No mutation in gelR was constructed in this report [3]. Yamazaki et al. report that strains with mutations in gene spsR were still mucoid, indicating that they produce polysaccharide, but the polysaccharide was not characterized as to rheology or attachment to the cell [9, 12].

Yamazaki described classical mutants of four *Sphingomonas* strains that produce polysaccharide as slime rather than attached to the cell [10]. Yamazaki did not describe how to screen mutagenized cultures for the slime phenotype. Yamazaki did not identify which gene or genes were mutated.

Sa-Correia reviewed work done on isolation of genes for gellan synthesis [8]. Sa-Correia described partial sequencing of some genes including urf32 and urf26 (equivalent to gelM and gelN described in Harding et al. [3]). The complete sequences of these genes were deposited in GenBank in April 2003 (GenBank Accession number AY242074). No function of these genes is reported. In the GenBank submission, genes urf32 and urf26 were merely designated as putative membrane protein and putative exported protein, respectively. No sequence for gelI or gelR was deposited.

Coleman describes the isolation of genes for diutan biosynthesis and investigation of some gene functions [1]. The dpsM and dpsN genes, which were designated by Coleman as orf3 and orf4, were described, but functions were not indicated.

A cluster of genes for biosynthesis of the S-88 polysaccharide from *Sphingomonas* strain ATCC 31554 was described [9, 12]. The functions of genes urf32 and urf26 (homologs of dpsM, gelM and dpsN, gelN), and spsI (homolog of gelI, dpsI) were not described. Gene spsR (homolog of gelR, dpsR) was described as encoding a protein remotely similar to bacterial and fungal polysaccharide lyases. The DNA sequences were deposited in GenBank (Accession number U51197).

There is a continuing need in the art to improve methods of making industrially useful sphingans and the properties of the sphingans.

SUMMARY OF THE INVENTION

According to one embodiment of the invention, a method is provided of making a bacterium. The bacterium is of the genus *Sphingomonas* and comprises a mutation in one or more genes selected from the group consisting of genes M, N, I, or R of the sphingan polysaccharide biosynthetic gene cluster. The M and N genes are also referred to in some publications as genes urf32, urf26, respectively, for unknown reading frame [8, 9]. A segment of genomic DNA of a first bacterium of the genus *Sphingomonas* is isolated. The segment comprises all or part of genes M and/or N, or I, or R of the sphingan polysaccharide biosynthetic gene cluster. A mutation in the segment is induced to form a mutated segment. The mutated segment is introduced into a second bacterium of the genus *Sphingomonas*. The second bacterium comprises wild-type genes M and/or N, or I, or R of the sphingan polysaccharide biosynthetic gene cluster. A progeny of the second bacterium in which the mutated segment has integrated in the genome and replaced wild-type genes M and/or N, or I, or R of the sphingan polysaccharide biosynthetic gene cluster of the second bacterium is isolated. The *Sphingomonas* bacterium may or may not be *S. elodea*.

According to another embodiment of the invention, another method is provided of making a bacterium of the genus *Sphingomonas* which comprises a mutation in one or more genes selected from the group consisting of genes M, N, I, and R of the sphingan polysaccharide biosynthetic gene cluster. Two non-contiguous segments of genomic DNA of a first bacterium of the genus *Sphingomonas* are isolated. The segments flank or include genes M and N of the sphingan polysaccharide biosynthetic gene cluster. Similarly, segments flanking gene I or gene R can be isolated. The two non-contiguous segments are ligated together. The ligated non-contiguous segments are introduced into a second bacterium of the genus *Sphingomonas*. The second bacterium comprises wild-type genes M and/or N, or I, or R of a sphingan polysaccharide biosynthetic gene cluster. A progeny of the second bacterium in which the ligated segment has integrated in the genome and replaced wild-type genes M and/or N, or 1, or R of a sphingan polysaccharide biosynthetic gene cluster of the second bacterium is isolated. The *Sphingomonas* bacterium may or may not be *S. elodea*.

According to yet another embodiment of the invention, a composition is provided. The composition comprises a native gellan polysaccharide with gel strength greater than that of an equivalent weight of native gellan from a capsular strain.

According to yet another embodiment of the invention, a composition is provided. The composition comprises a diutan polysaccharide which imparts to a fluid an increased viscosity relative to an equivalent weight of diutan produced by strain ATCC 53159.

According to another embodiment of the invention, an isolated and purified bacterium of the genus *Sphingomonas* is provided. The bacterium comprises a deletion in one or more genes selected from the group consisting of genes M, N, I, and R of the sphingan polysaccharide biosynthetic gene cluster. The bacterium can be cultured in a culture medium under conditions suitable for producing sphingan polysaccharide to produce sphingan polysaccharide in the culture medium. The culture broth of the bacterium can be used directly as a viscosifier or gelling agent, or after precipitation with alcohol. Alternatively, the culture broth can be subjected to a procedure to remove bacteria from the culture broth prior to use as a viscosifier or gelling agent or recovery from the broth. The *Sphingomonas* bacterium may or may not be *S. elodea*.

These and other embodiments which will be apparent to those of skill in the art upon reading the specification provide the art with new methods, strains, and compositions for making viscosifiers and gelling agents.

BRIEF DESCRIPTION OF THE DRAWINGS

FIG. 4. Sequence of DNA at the site of deletion of dpsN (SEQ ID NO: 19), and amino acid sequence of the fusion peptide (SEQ ID NO: 20).

DETAILED DESCRIPTION OF THE INVENTION

Figure 1:
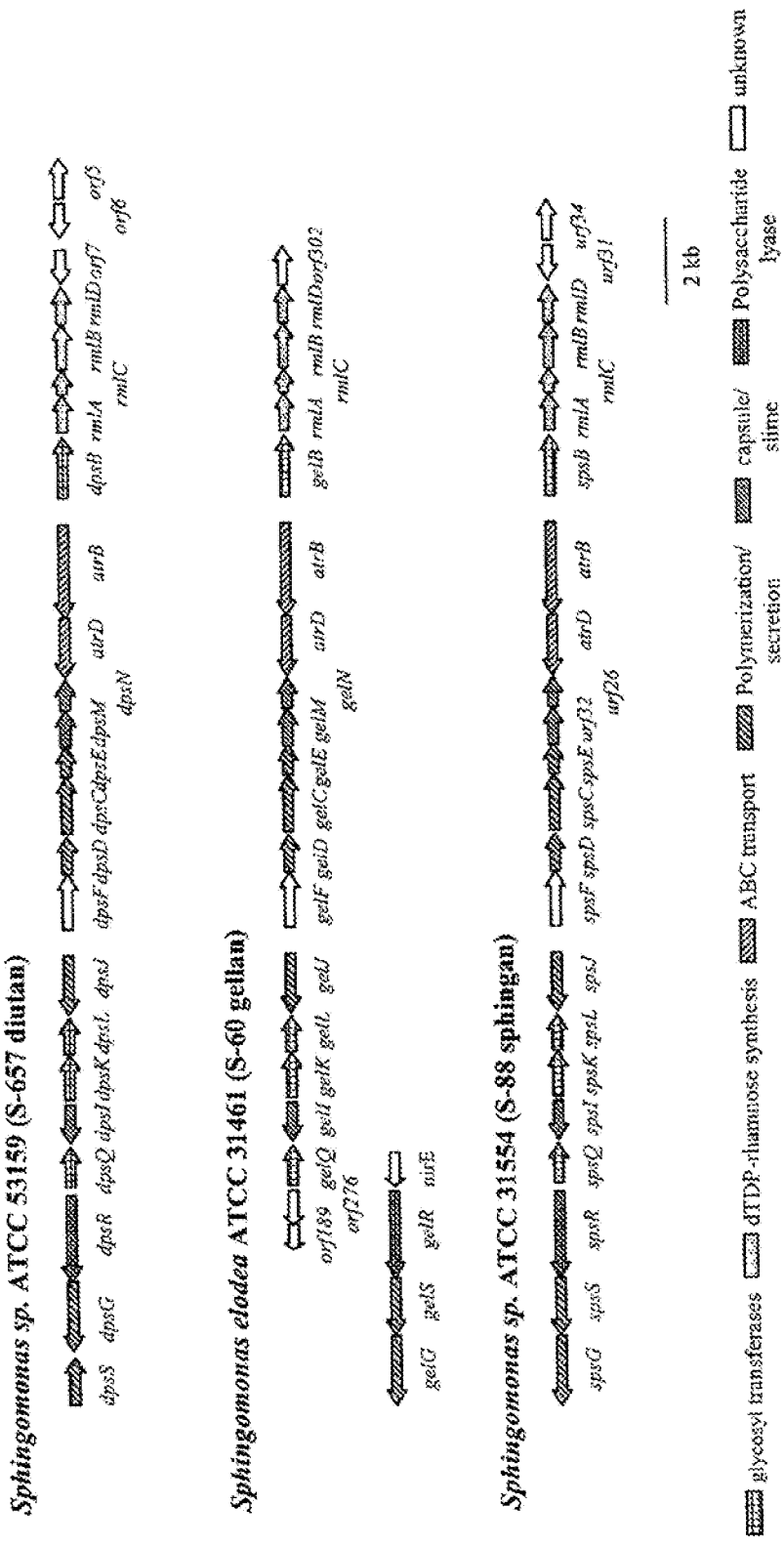
FIG. 1. Comparison of gene clusters for polysaccharide biosynthesis in *Sphingomonas* strains ATCC 31554, ATCC 31461 and ATCC 53159.

Genes have been identified that control the attachment of polysaccharide to bacterial cells in two *Sphingomonas* strains. Deletion of either one or both genes gelM (dpsM) and gelN (dpsN) or inactivation of gelI results in polysaccharide being released into the medium as slime rather than attached to the cell surface as capsular polysaccharide. Formation of slime form of polysaccharide eases handling of bacterial cultures, improves mixing during fermentation, may increase production, and in some cases improves rheology of the polysaccharide. Site directed mutagenesis is advantageous over random mutagenesis and screening for slime-forming mutants for many reasons, including speed and avoidance of unrelated mutations. Inactivation of the gene gelR was found to improve the rheology (gel strength) of the slime form of gellan polysaccharide.

Orthologs of dpsM, dpsN, gelM, gelN, and gelI can be inactivated in any *Sphingomonas* strain to obtain the slime-forming phenotype. Orthologs of gelR can be inactivated to prevent degradation of the polysaccharide resulting in improved rheology. Suitable Sphingomonads include without limitation those which make rhamsan (ATCC 31961), welan (ATCC 31555), gellan (ATCC 31461), and diutan (ATCC 53159) and strains making polysaccharides S7 (ATCC 21423), S88 (ATCC 31554), S198 (ATCC 31853) and NW11 (ATCC 53272). The ATCC numbers refer to the deposit numbers of the strains at the American Type Culture Collection. These are exemplified by *S. elodea* ATCC 31461 and *Sphingomonas* sp. ATCC 53159, but other strains can be used. Suitable Sphingomonads which can be used include *Sphingomonas adhaesiva, Sphingomonas aerolata, Sphingomonas alaskensis, Sphingomonas aquatilis, Sphingomonas aromaticivorans, Sphingomonas asaccharolytica, Sphingomonas aurantiaca, Sphingomonas capsulata, Sphingomonas chlorophenolica, Sphingomonas chungbukensis, Sphingomonas cloacae, Sphingomonas echinoides, Sphingomonas elodea, Sphingomonas faeni, Sphingomonas herbicidovorans, Sphingomonas koreensis, Sphingomonas macrogoltabidus, Sphingomonas mali, Sphingomonas melonis, Sphingomonas natatoria, Sphingomonas parapaucimobilis, Sphingomonas paucimobilis, Sphingomonas pituitosa, Sphingomonas pruni, Sphingomonas rosa, Sphingomonas sanguinis, Sphingomonas sp., Sphingomonas stygia, Sphingomonas subarctica, Sphingomonas suberipciens, Sphingomonas subterranea, Sphingomonas taejonensis, Sphingomonas terrae, Sphingomonas trueperi, Sphingomonas ursincola, Sphingomonas wittichii, Sphingomonas xenophaga, Sphingomonas yabuuchiae,* and *Sphingomonas yanoikuyae*. Orthologs can be identified on the basis of gene location and organization in a sphingan biosynthetic gene cluster, on the basis of overall homology, and/or on the basis of domain homology. Typically, the level of overall homology will be greater than 44%, often greater than 55%, 66%, 77%, 88%, or 98% with one of the dpsM, dpsN, gelM, gelN, gelI, or gelR genes. An ortholog desirably has homology greater than 80% with at least one of these four genes.

Site directed mutagenesis can be used to make mutations in a desired known target gene or genomic region. This eliminates the trial-and-error nature of random induced mutagenesis or spontaneous mutagenesis. Formation of deletions insures that the mutations will not revert, as is possible with point (substitution) mutations and insertion mutations, for example. Deletions also have the benefit of not employing exogenous DNA, such as drug resistance markers or other environmentally undesirable markers.

An isolated segment of genomic DNA comprising the M and/or N, I, or R of the sphingan biosynthetic gene cluster or flanking DNA is DNA that is not connected to genomic DNA to which it is normally attached. Isolated DNA can be obtained by purification from natural sources, by synthesis, or by amplification, as non-limiting examples. The isolated DNA will typically be on a fragment of DNA in vitro, but isolated DNA could also be on a vector, such as a plasmid or transducing phage, which contains the desired portion of the *Sphingomonas* genome. Flanking DNA is typically from the genomic regions immediately adjacent to the M and/or N, I, or R within about 500 bp of the genes, or within about 1-2 kb of the genes.

Any method known in the art can be used to introduce a mutation into an isolated segment comprising all or part of genes M and/or N, I, or R of the sphingan biosynthetic gene cluster. A deletion can be introduced using restriction endonucleases, for example, and rejoining formerly non-contiguous nucleotides. A deletion can be formed by amplifying and joining two non-contiguous segments of the genes or two non-contiguous segments of DNA flanking the target gene. An insertion can be made in an isolated segment using endonuclease digestion and ligation. Chemical mutagenesis can be used on an isolated segment of genomic DNA. Any mutagenesis method can be selected and used according to the particular circumstances.

After mutations have been induced, the segment of genomic DNA can be reintroduced into a recipient bacterium. Typically, but not necessarily, the recipient will be of the same species as the donor of the segment. Any method known in the art for introducing exogenous DNA into a bacterium can be used. Suitable methods include without limitation electroporation, conjugation, spheroplast formation, calcium chloride precipitation and transformation, liposomes, and viral transduction. Any nucleic acid introduction method can be selected and used according to the particular circumstances.

If the segment of mutated genomic DNA introduced into the recipient bacterium does not have a means of replicating itself, then it must integrate into a replicon in the recipient bacterium in order to be maintained. Typically such an integration event will integrate the entire incoming plasmid. One can detect a marker on the introduced DNA to identify that the DNA has integrated. In order to detect resolution of the integrate, one can screen or select for loss of a marker on the introduced DNA. Suitable markers for accomplishing this are known in the art, and any can be used as the circumstances dictate. To determine the isolates in which the introduced version of the sphingan genes replaces the wild-type version in the recipient, the size or sequence of the DNA can be determined, for example, by PCR.

As demonstrated below, the slime form of sphingan produced for example by a sphingan biosynthetic gene cluster gene M and/or N, mutant may have improved rheological properties over the form which is attached to bacterial cells. Such improved rheological properties are reflected in the ability of the same weight of material to provide more viscosifying power. Such improvement may be modest, such as at least 5% 10%, 15%, 20% or 25%, or it can be more substantial, with an improvement of at least 30%, 40%, 50%, 60%, 70%, 80%, or 90% relative to the sphingan produced by the capsule-forming parent. Rheologically properties can be measured using any technique which is known in the art. Suitable techniques include without limitation the measurement of Low Shear Rate Viscosity ("LSRV") in tap water solutions and the measurement of Sea Water Viscosity ("SWV") in high salt solutions.

The slime form of gellan, produced, for example, by a gelN mutant in combination with a mutation in the putative lyase gene, gelR, results in formation of gellan of high gel strength. The gel strength will typically be greater than 1000, whereas the capsular strain typically produces a gellan with gel strength of 700-900, but less than 1000.

Purified bacteria according to the present invention are those which have been microbiologically purified, for example using liquid dilution techniques or streaking on solid media to form single colonies. Standard techniques known in the art of microbiology can be used for this purpose.

Mutants according to the present invention can be cultured and grown using the same or similar techniques as used for the parental strains. Liquid culture properties of the mutants may be improved, permitting increased aeration and mixing. The culture broth of the mutant may also provide more efficient recovery than with the attached form of polysaccharide. In addition, the mutants may also provide a product with improved clarity relative to the attached form of polysaccharide. Bacteria may optionally be removed from the polysaccharide produced by the mutant by filtration, centrifugation, or by sedimentation. The culture broth can be chemically, enzymatically, or thermally (hot or cold) treated before or after bacteria removal, as desired.

The genes from *S. elodea* ATCC 31461 involved in gellan attachment to the cell surface are gelM and gelN (FIG. 1; SEQ ID NO: 13) and gelI (FIG. 1, SEQ ID NO: 25). A strain has been constructed that has a deletion of most of genes gelM and gelN, resulting in the slime-forming phenotype. A specific deletion of gelN has also been constructed, and an insertion in gene gelI. Both of these mutations result in the slime-forming phenotype. The coding sequences of gelM and gelN are at nucleotides 501-1382 and 1366-2064, respectively, in SEQ ID NO: 13. The encoded amino acid sequences are shown in SEQ ID NOs: 16 and 15, respectively. The coding sequences of gelI is at nucleotides 501 to 1403, respectively, in SEQ ID NO: 25. The encoded amino acid sequences are shown in SEQ ID NO: 26. A deletion of gene gelR was found to result in improved gel strength for gellan in the slime form. The coding sequences of gelR is at nucleotides 478 to 2457, respectively, in SEQ ID NO: 27. The encoded amino acid sequences are shown in SEQ ID NO: 28.

The genes from *Sphingomonas* sp. ATCC 53159 involved in diutan attachment to the cell surface are dpsM and dpsN (FIG. 1; SEQ ID NO: 14), and presumably dpsI based on homology to gelI. Deletions of each of genes dpsM and dpsN have been constructed and both result in the slime-forming phenotype. The coding sequences of dpsM and dpsN are at nucleotides 456-1337 and 1321-2019, respectively, in SEQ ID NO: 14. The encoded amino acid sequences are shown in SEQ ID NOs: 18 and 17, respectively.

It will be apparent to those skilled in the art that the same or similar methods used for gellan synthesis may also be used for diutan synthesis. Thus, mutations in genes dpsI and dpsR could readily be constructed. The coding sequences of dpsI is at nucleotides 501-1472, respectively, in SEQ ID NO: 29. The encoded amino acid sequences are shown in SEQ ID NO: 30. The coding sequences of dpsR is at nucleotides 501-2498, respectively, in SEQ ID NO: 31. The encoded amino acid sequences are shown in SEQ ID NO: 32.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

Production of Gellan Slime-Forming Mutants

For construction of mutants of *Sphingomonas elodea*, a derivative of ATCC 31461 designated S60 wtc[1] was used, which has improved uptake of DNA. This strain can be readily made by one skilled in the art. PCR amplification was used to amplify regions flanking the gelM-gelN genes [3]. The amplified fragments were cloned into the pLO2 vector and introduced into S60 wtc by conjugation to replace the gelM and gelN genes on the genome with the deletion, by double crossover homologous recombination. Vector pLO2 does not replicate in S60 wtc, so initial selection for kanamycin resistance selects for those colonies in which the plasmid has integrated into the chromosome by homologous recombination. The vector also contains the gene sacB. This gene confers sensitivity to sucrose. Thus, selection on sucrose can be used to detect isolates that have lost the plasmid and retain one copy of the deletion or wild-type genes.

*S. elodea* ATCC 31461 has a low efficiency of uptake of DNA, particularly large plasmids (about $10^{-7}$). Spontaneous mutants of ATCC 31461 with increased efficiency of DNA uptake were isolated. It was suspected that those few cells that were successful recipients of a plasmid, such as the broad-host-range plasmid pLAFR3, represented mutants in the recipient population with an increased ability to take up this plasmid DNA. To allow loss of the plasmid, three transconjugants containing pLAFR3 were grown under nonselective conditions (i.e., without tetracycline antibiotic) with serial passage for about 30 generations. Three independent plasmid-cured strains (i.e., tetracycline-sensitive derivatives from each of the initial transconjugants) were tested and all three exhibited increased conjugation frequency ($4.2 \times 10^{-3}$, $0.6 \times 10^{-2}$, and $1.5 \times 10^{-2}$), representing a $10^5$-fold increase compared to the wild-type strain. This increased conjugation frequency was stable and reproducible. One of these strains was designated S60 wtc [3].

A plasmid containing the gelM-gelN deleted region was introduced into S60 wtc by tri-parental conjugal mating, using pRK2013 to provide transfer functions, and transconjugants selected on YM-Sm (25 ug/ml)-Km (7.5 ug/ml) medium. Streptomycin prevents growth of the *E. coli* strains. Kanamycin resistant plasmid integrants were isolated. Sucrose sensitivity was used to select for a second recombination event which eliminated the vector. Five isolates were passed two times under non-selective conditions, i.e., without antibiotic. Aliquots were then plated on medium with 8% sucrose. Sucrose resistant colonies were isolated and tested for kanamycin sensitivity. Genomic DNA was isolated and PCR was used to determine which Kms isolates had retained the deletion. An amplified fragment of the expected size for a deletion resulted from the genomic DNA from four strains. These four deletion strains were purified on YM medium. All four strains appeared less mucoid, softer, flatter and darker yellow than the wild type.

Example 2

Characterization of gelM-gelN Deletion Strains

The gelM-gelN deletion isolates were evaluated in shake flask fermentations. The ΔgelM-gelN culture broth was fluid and smooth compared to the more solid, viscous S60 wtc broth. Precipitation with isopropyl alcohol produced longer, thicker, fibers from the mutant strains compared to S60 wtc fibers. However, the deletion mutants had 22% reduction in yield of total precipitable material and produced only 30% of the broth viscosity of wild-type. The gellan produced had a normal composition of sugars, and glyceryl and acetyl substituents.

Figure 2:
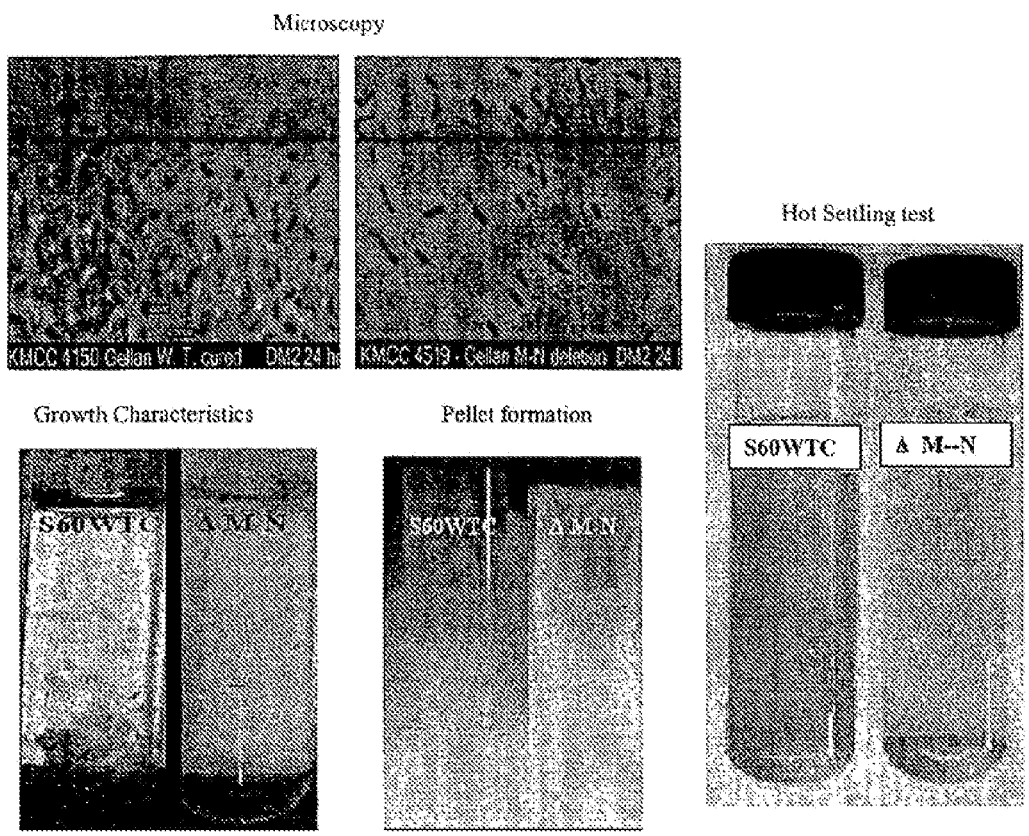
FIG. 2. Slime forming characteristics of S60WTC gelM-gelN mutants

The mutants were evaluated for slime forming characteristics, using several techniques, including microscopic evaluation, cell clumping, cell pellet formation, and hot settling test, as shown in FIG. 2.

The hot settling test consisted of heating the gellan broth in the autoclave for ten minutes to melt the gellan, then transferring the hot broth to a large test tube and incubating overnight at 95° C. (to maintain broth as liquid). With a capsular strain, the cells are attached to the polysaccharide and remain suspended. For slime-formers, the cells are not attached and settle during overnight incubation. The gelM-gelN deletion strains were shown to be slime formers by this test.

For the centrifugation test, the strains were grown overnight in DM2 media containing 1% glucose and centrifuged at maximum speed in the Eppendorf centrifuge. Inactivation of gelM-N genes results in complete loss of attachment of the polysaccharide from the cell surface such that the cells can be pelleted by centrifugation.

By microscopic evaluation, most of the S60 wtcΔgelM-N cells are free and motile, whereas the S60 wtc are in the gum matrix. In cell culture, the S60 wtcΔgelM-N cells grow in suspension, whereas S60 wtc cells form clumps.

Example 3

Construction of Gellan Slime-Forming Mutants

A deletion was constructed of gelN for gellan biosynthesis. PCR primers were designed to amplify DNA fragments upstream (500 bp) and downstream (401 bp) of the gelN gene [3]. Primers used are shown in Table 1.

TABLE 1

Primers for construction of gelN deletion mutant.

| Primer | Sequence | Purpose |
|---|---|---|
| SacI-GelN primer 1 | 5' *TGGAGCTC*-GGTGCTGTGGTTGTTCTT 3' (SEQ ID NO: 1) | Amplifies 500 bp upstream of gelN |
| XbaI-GelN primer 2 | 5' *GGTCTAGA*-GTCAGGCCGGTTGAACAT 3' (SEQ ID NO: 2) | |

TABLE 1-continued

Primers for construction of gelN deletion mutant.

| Primer | Sequence | Purpose |
|---|---|---|
| XbaI-GelN primer 3 | 5' AG*TCTAGA*-GCCTGAACGCCGAAAGGG 3'<br>(SEQ ID NO: 3) | Amplifies 401 bp downstream of gelN |
| SphI-GelN primer 4 | 5' GTT*GCATGC*-CGTGATGGTGGACAATGG 3'<br>(SEQ ID NO: 4) | |

Primers SacI-GelN primer 1 and XbaI-GelN primer2 were used to amplify a 500 bp fragment from the gelM gene as a SacI-XbaI fragment (total 516 bp). Primers XbaI-GelN primer3 and SphI-GelN primer4 were used to amplify a 401 bp fragment from the atrD gene as an XbaI-SphI fragment (total 418 bp). Since the end of the gelM gene overlaps the start of the gelN gene by 17 bp, the stop codon of gelM and the start codon of gelN were retained, as well as the natural stop codon of gelN. The PCR fragments were ligated sequentially into the polylinker of plasmid vector pLO2 [4], resulting in clone pLO2-gelNdeln#1 carrying the deletion of gelN.

Plasmid pLO2-gelNdeln#1 was then used to transfer the deletion to strain S60 wtc$^3$ by conjugation and homologous recombination. Strain S60 wtc is a strain derived from ATCC 31461 as a spontaneous mutant with increased ability to take up plasmid DNA [2]. A chromosomal integrant was selected by kanamycin resistance. Subsequent growth for approximately 30 generations in the absence of antibiotic allowed for excision of the plasmid. Recombinants that had lost the plasmid were then selected by sucrose (8%) tolerance, due to loss of the plasmid-encoded sacB gene, and then colonies were screened for kanamycin sensitivity. The sacB gene encodes an enzyme levansucrase for synthesis of levan from sucrose. Levan is toxic to the cells. Cells that have lost the sacB gene can grow on sucrose. The sucrose tolerant isolates can be wild-type or deletion. Genomic DNA was prepared from several isolates to identify those isolates that had retained the gelN deletion versus the wild-type gene, as determined by PCR. Isolates with the gelN deletion had softer, more watery colonies compared to the hard colonies of the wild-type gelN+isolates (See above discussion regarding use of mutant with increased ability to take up DNA).

Example 4

Characterization of gelN Deletion Mutants

Figure 3:
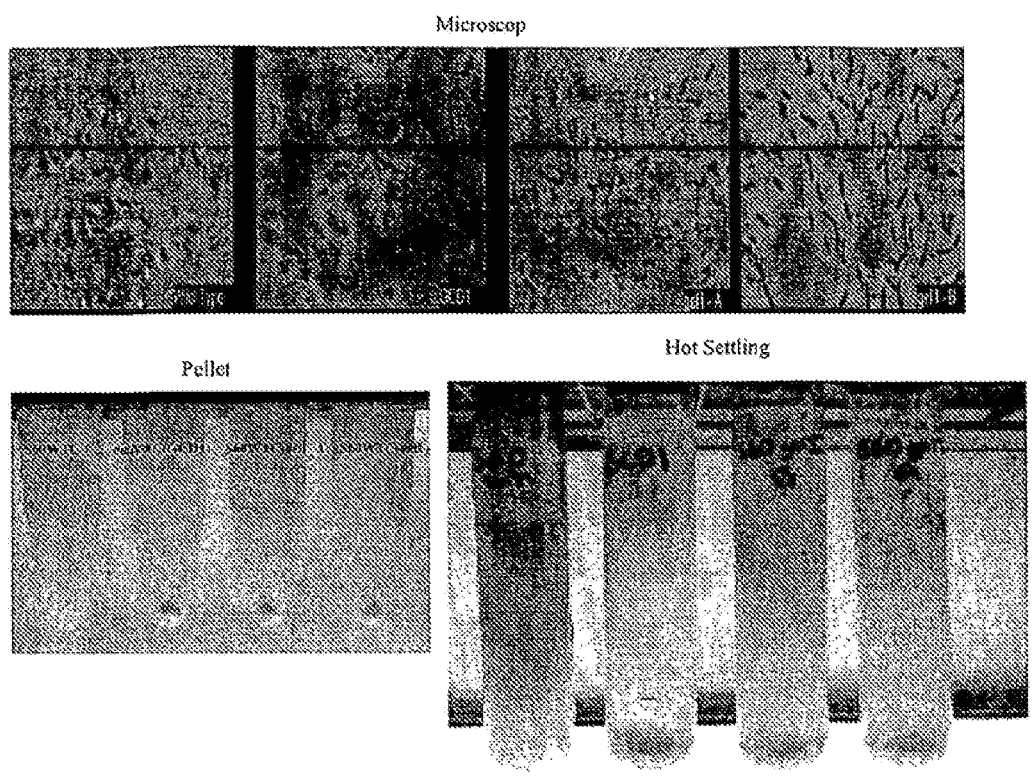
FIG. 3. Slime forming characteristics of S60WTC gelN and gelI Mutants

The gelN deletion mutants had similar properties to the gelM-gelN deletion mutants. Cells were readily pelleted by centrifugation. In cell culture, the gelN deletion mutants grew in suspension, whereas the wild-type cells formed clumps. Thus, inactivation of the gelN gene can result in the slime phenotype as shown in FIG. 3.

Five individual isolates of gelN deletion mutants were evaluated in shake flask fermentations. The average yield (total precipitable material, TPM) for the gelN mutants (1.10 g/100 ml) was comparable to that of the S60 wtc control (1.08 g/100 ml). Selected gelN mutants were evaluated in 20 L Applikon fermentors using media containing organic and inorganic nitrogen, salts and corn syrup. Gellan polysaccharide was precipitated with isopropyl alcohol, dried and weighed. Average yield of total precipitable material for the mutants was 94% of that of the wild-type control, however, the broth viscosity was decreased by about 40%. This decrease in broth viscosity facilitates mixing in the fermentors.

TABLE 2

Fermentation characteristics of gelN mutants

| Strain | TPM<br>g/L | Broth Viscosity<br>Cp |
|---|---|---|
| Wild-type | 12.80 | 5500 |
| gelN #1 | 12.04 | 3850 |
| gelN #2 | 12.15 | 2700 |
| gelN #4 | 11.80 | 3400 |
| average | 12.00 | 3317 |

Viscosity was measured in the Brookfield LVF viscometer using the No. 4 spindle at 60 rpm.

Example 5

Construction of Mutants Producing Gellan Slime with Improved Quality

The slime mutants of gellan had lower broth viscosity, as described in Example 4, which facilitates mixing in the fermentors. Gellan polysaccharide forms a gel after heating and cooling, and gellan is used in various food applications due to its unique textural and rheological properties. Therefore, the gel strength of the gellan produced by the slime mutants was evaluated. The gel strength is determined by the break or fracture of a prepared gel surface with a plunger.

The gellan fermentation broth was adjusted to pH 4.6 (to prevent deacylation) and pasteurized by heating to about 100° C. for several minutes. Gellan product was precipitated by addition of three times volume of isopropyl alcohol, and the fibers dried at 60° C. for two hours and milled.

A calcium solution was prepared by adding 2 ml of a 0.3 M CaCl$_2$.2H$_2$O stock solution to 295 ml of deionized water in a tared 600 ml stainless steel beaker. While stirring the solution at 700 rpm, 3.0 g of gellan product was added and allowed to disperse for 1 to 2 minutes. The beaker was placed into a preheated water bath at 94-95° C. for four minutes, covered and heated for 15 minutes, then stirred for 3 minutes. Solution weight was adjusted to 300 g with heated deionized water, mixed and then left standing at 94-95° C. Solution was transferred into six ring molds (0.5 inch height, 1.375 inch outer diameter, 0.125 inch wall thickness) and covered with a plastic cover plate and allowed to cool at room temperature (20-21° C.) for 20 to 24 hours. The disc was removed from the mold onto a plexiglass plate. Gel strength, or force to break (recorded in g/cm$^2$) was determined in a TA-TX2 Texture Analyzer with a Kobe plunger (TA-19) at 1.0 mm/s.

Gellan from the slime mutants had lower gel strength than that from the wild-type capsular stain, as shown in Table 4. This result was in contrast to mutants of ATCC 53159 that produce the slime form of diutan, which had improved rheology as described in Example 11, It was considered possible that the slime form of gellan may be degraded by a gellan lyase enzyme, produced by *S. elodea*. Therefore, a strain was constructed that has a deletion of a gene, gelR, which produces a protein with homology to polysaccharide degrading proteins, e.g. lyases.

The gelR deletion was constructed in *S. elodea* strain S60 wtc and strain GBAD-1 [11]. PCR primers were designed to amplify DNA fragments upstream (502 bp) and downstream (435 bp) of the gelR gene. PCR primers used are shown in Table 3.

TABLE 3

Primers used for construction of gelR deletion

| Primer | Sequence | Purpose |
|---|---|---|
| SacI-GelR primer 1 | 5' ACGAGCTCAGATCAGCCGCAACCTCCT 3' (Seq ID No: 21) | Amplifies 486 bp upstream of gelR |
| XbaI-GelR primer 2 | 5' GCTCTAGA-CGCCGCCATGTTAATCACC 3' (Seq ID No: 22) | |
| XbaI-GelR primer 3 | 5' GCTCTAGA-GATGCGTTCCACGCCTGAC 3' (Seq ID No: 23) | Amplifies 419 bp downstream of gelR |
| SphI-GelR primer 4 | 5' ATGCATGC-CGATCGCGCTCATCAGGGT 3' (Seq ID No: 24) | |

Primers SacI-GelR primer 1 and XbaI-GelR primer 2 were used to amplify a 498 bp fragment upstream of gelR as a SacI-XbaI fragment (total 502 bp). Primers XbaI-GelR primer 3 and SphI-GelR primer 4 were used to amplify a 419 bp fragment downstream of gelR as an XbaI-SphI fragment (total 435 bp). The PCR fragments were digested with restriction enzymes and ligated sequentially into the polylinker of plasmid vector pLO2 [4] resulting in clone pLO2-gelRdeletn#4, carrying the deletion of gelR.

Plasmid pLO2-gelRdeletn#4, which cannot replicate in *Sphingomonas*, was transferred into *S. elodea* strains S60 wtc and GBAD-1 by conjugation from *E. coli* DH5α, using helper plasmid pRK2013 that supplies transfer functions [2]. Chromosomal integrants were selected by kanamycin resistance on yeast extract-malt extract (YM) medium with kanamycin and streptomycin (to counterselect *E. coli*). Subsequent growth of the *Sphingomonas* integrants for approximately 30 generations in the absence of antibiotic allowed for the excision of the plasmid. Recombinants that had lost the plasmid were selected by sucrose tolerance due to loss of the plasmid encoded sacB gene, and colonies screened for kanamycin sensitivity. PCR was used to test which isolates had retained the gelR deletion.

The gelN deletion was than transferred into the gelR deletion mutant of the GBAD-1 strain as described above in Example 3. Plasmid pLO2-gelNdeln#1 was used to transfer the gelN deletion into GBAD gelR by conjugation and homologous recombination. A chromosomal integrant was selected by kanamycin resistance on YM agar with Km (20 ug/ml) and Sm (25 ug/ml). Subsequent growth in the absence of antibiotic allowed for excision of the plasmid. Recombinants that had lost the plasmid were selected by sucrose tolerance due to loss of the plasmid-encoded sacB gene, and then colonies were screened for kanamycin sensitivity.

The gelR deletion mutants exhibited different colony morphology than the wild-type strains. The gelR deletion strains had smaller rough gummy colonies compared to larger smooth gummy colonies with transparent edges for the gelR+ of S60 wtc or GBAD-1. The gelN-gelR deletion mutants had colony morphology similar to the gelN slime mutants.

Example 6

Characterization of GelN-GelR Mutants

These strains were evaluated in 20 L Applikon fermenters using media containing organic and inorganic nitrogen, salts and corn syrup. Gellan polysaccharide was precipitated with isopropyl alcohol, dried and weighed. Gel strength was determined by the method described in Example 5. The GBAD-1 gelN-gelR strain produced gellan of higher gel strength than the gellan produced from the gelN slime mutants or the wild-type capsular strains.

TABLE 4

Rheological characterization of gellan from mutants

| Strain | Phenotype | n = | Aver TPM % of wild-type | Aver. Broth Visc cP | Aver Gel strength |
|---|---|---|---|---|---|
| S60wtc | capsule | 3 | — | 7292 | 411 |
| GBAD1 | capsule | 1 | 91 | 4600 | 629 |
| GelN mutants | slime | 7 | 93 | 2900 | 132 |
| GBADlgelRgelN | slime | 3 | 96 | 5083 | 1447 |

Example 7

Construction of GelI Mutant

An insertion mutation in gene gelI was constructed. PCR primers were designed to amplify an internal fragment of the gelI gene [3]. The amplified fragment was cloned into the pLO2 plasmid vector and introduced into S60 wtc by conjugation, selecting on YM-Sm (25 μg/ml)-Km (7.5 μg/ml) medium. Selection for kanamycin resistance selects for those transconjugants that have the plasmid inserted by homologous recombination into the gelI gene, thus inactivating this gene. The gelI mutant had altered colony morphology, similar to that of the gelM-gelN and the gelN deletion strains, i.e. mucoid but softer colonies.

Example 8

Characterization of GelI Mutant Strain

The gelI mutant was evaluated in shake flask fermentation. The mutant had less viscous broth compared to the wild-type strain and about a 20% reduction in yield of total precipitable material. The gellan produced had a normal composition of sugars and glyceryl and acetyl substituents [3].

The gelI mutant was evaluated for slime forming characteristic using several techniques including microscopic evaluation, cell clumping, cell pellet formation and hot settling test as described above. The gelI insertion mutant had similar characteristics to the gelM-gelN and the gelN deletion mutants. Microscopic evaluation showed that the cells were free and motile. In cell culture, the gelI mutants grew in suspension rather than clumps. Cells were readily pelleted from $DM_2$ medium by centrifugation. Cells also settled well in the hot settling test. Thus, the mutation in the gelI gene also results in the slime phenotype, as shown in FIG. 3.

Example 9

Production of Diutan Slime-Forming Mutants

*Sphingomonas* sp. ATCC 53159 (S-657) produces a polysaccharide (diutan) with a structure similar to that of gellan (i.e., it has a glucose-glucuronic acid-glucose-rhamnose repeat unit), but with a side chain of two rhamnose residues attached to one glucose residue. Diutan has two acetyl substituents, and lacks glyceryl groups. Diutan is useful as a viscosifier in oil field and cement applications. *Sphingomonas* strains produce polysaccharides as capsules firmly bound to the cell surface. The exact mechanism of attachment is not known. The capsule may limit productivity by impairing oxygen uptake. The functionality of the polysaccharide may be hindered by its being attached to the cell rather than free in solution.

Strain Construction:

Deletions of the corresponding genes dpsM and dpsN of *Sphingomonas* sp. ATCC 53159, which produces diutan (S-657), were constructed. Each gene was deleted independently and the effect on capsule to slime determined. Briefly, PCR was used to amplify two fragments homologous to DNA flanking the target gene. These fragments were cloned into a narrow-host-range plasmid pLO2 that cannot replicate in *Sphingomonas* and contains two selective markers, $kan^R$ and sacB. Selection for kanamycin resistance selects for cells in which the plasmid has integrated into the chromosome in one of the homologous regions. The kanamycin resistant strain was then grown under nonselective conditions to allow loss of the plasmid by a second recombination. Loss of plasmid was selected by tolerance to sucrose. The sacB gene encodes an enzyme levansucrase for synthesis of levan from sucrose. Levan is toxic to the cells. Cells that have lost the sacB gene can grow on sucrose. The sucrose tolerant isolates can be wild-type or deletion. Presence of the deletion was confirmed by PCR. Mutants were tested for slime or capsule production. No foreign DNA, plasmid, or antibiotic resistance genes remained in the final strain.

Detailed Construction of dpsN and dpsM Deletions Strains

Deletions of dpsM and dpsN were constructed on a plasmid and transferred to the genome of ATCC 53159, using a gene replacement strategy similar to that described for *S. elodea* deletion mutants [3]. PCR was used to amplify DNA regions flanking the target gene and then the fragments cloned into plasmid pLO2 [4], which was then used to exchange the deletion for the target gene in the chromosome. Primers used for the PCR are shown in Table 5. Restriction sites for cloning (shown in italics) were added to the ends of the primers.

TABLE 5

Primers for construction of deletion mutations.

| Primer | Sequence | Purpose |
|---|---|---|
| SacI-DpsN primer 1 | 5' TTGAGCTC-GCTGTGGCTGTTCTTCCT 3' (SEQ ID NO: 5) | Amplifies 497 bp upstream of dpsN |
| XbaI-DpsN primer 2 | 5' CG*TCTAGA*-GTCACGCCGGTTGAACAT 3' (SEQ ID NO: 6) | |
| XbaI-DpsN primer 3 | 5' TC*TCTAGA*-CTCGGTCACCAGGTCTGAA 3' (SEQ ID NO: 7) | Amplifies 396 bp downstream of dpsN |
| SphI-DpsN primer 4 | 5' CT*CGCATGC*-CGGTAAAGGTGAAG 3' (SEQ ID NO: 8) | |
| SacI-DpsM primer 1 | 5' TT*GAGCTC*-GATCGGCGTTAAGACTGC 3' (SEQ ID NO: 9) | Amplifies 474 bp upstream of dpsM |
| XbaI-DpsM primer 2 | 5' CG*TCTAGA*-TCATCGCGGTCGCTGCCAT 3' (SEQ ID NO: 10) | |
| XbaI-DpsM primer 3 | 5' CC*TCTAGA*-CGTCGGAGGCATCATGTTC 3' (SEQ ID NO: 11) | Amplifies 509 bp downstream of dpsM |
| SphI-DpsM primer 4 | 5' TC*GCATGC*-TCTGCTGATTGCCGTTCT 3' (SEQ ID NO: 12) | |

Deletion constructions were designed to leave the remaining genes for diutan synthesis intact. For the dpsN deletion, primers SacI-DpsN primer1 and XbaI-DpsN primer2 were used to amplify a 497 bp fragment from the dpsM gene as a SacI-XbaI fragment (total 513 bp). Primers XbaI-DpsN primer3 and SphI-DpsN primer4 were used to amplify a 396 bp fragment from the atrD gene as an XbaI-SphI fragment (total 413 bp). Since the end of the dpsM gene overlaps the start of the dpsN gene by 17 bp, the stop codon of dpsM and the start codon of dpsN were retained, as well as the natural stop codon of dpsN. Thus this construction may result in formation of a small peptide of 13 amino acids, as shown in FIG. 4. The PCR fragments were ligated sequentially into the polylinker of plasmid vector pLO2 [4], resulting in clone pLO2-dpsNdeln#3 carrying the deletion of dpsN.

This plasmid, pLO2-dpsNdeln#3 which cannot replicate in *Sphingomonas*, was transferred into the *Sphingomonas* strain ATCC 53159 by conjugation from *E. coli* DH5α using a helper plasmid pRK2013 that supplies transfer functions [2].

Chromosomal integrants were selected by kanamycin resistance on YM medium with 7.5 µg/ml kanamycin, and 25 µg/ml streptomycin (to counterselect *E. coli*). Subsequent growth of the *Sphingomonas* strains for approximately 30 generations in the absence of antibiotic allowed for excision of the plasmid. Recombinants that had lost the plasmid were then selected by sucrose (8%) tolerance, due to loss of the plasmid-encoded sacB gene, and then colonies screened for kanamycin sensitivity. Genomic DNA was prepared from several isolates to identify those isolates that had retained the dpsN deletion versus the wild-type gene, as determined by PCR.

Similarly, a deletion of dpsM was constructed. Primers SacI-DpsM primer1 and XbaI-DpsM primer2 were used to amplify a 474 bp fragment from the dpsE gene as a SacI-XbaI fragment (total 490 bp). Primers XbaI-DpsM primer3 and SphI-DpsM primer 4 were used to amplify a 509 bp fragment from the dpsN gene as a XbaI-SphI fragment (total 525 bp). Since the end of the dpsM gene overlaps the start of the dpsN gene by 17 bp, the stop codon of dpsM and the start codon of dpsN were retained. A stop codon was incorporated within the XbaI cloning site. A 7-amino acid peptide may be formed from the dpsM start site. The PCR fragments were ligated sequentially into the polylinker of plasmid vector pLO2 [4], resulting in clone pLO2-dpsMdeln#1 carrying the deletion of dpsM. This plasmid was transferred by conjugation into ATCC 53159 selecting for kanamycin resistant integrants, followed by growth in the absence of antibiotic and detection of sucrose tolerant, kanamycin sensitive recombinants. Genomic DNA was isolated from selected recombinants and screened by PCR for presence of the deletion.

Example 10

Characterization of Diutan Slime-Forming Mutants

Results of several tests showed that both the dpsM and dpsN deletions result in a change from capsule former to slime former, as shown in FIGS. 3 and 4.

Figure 5:
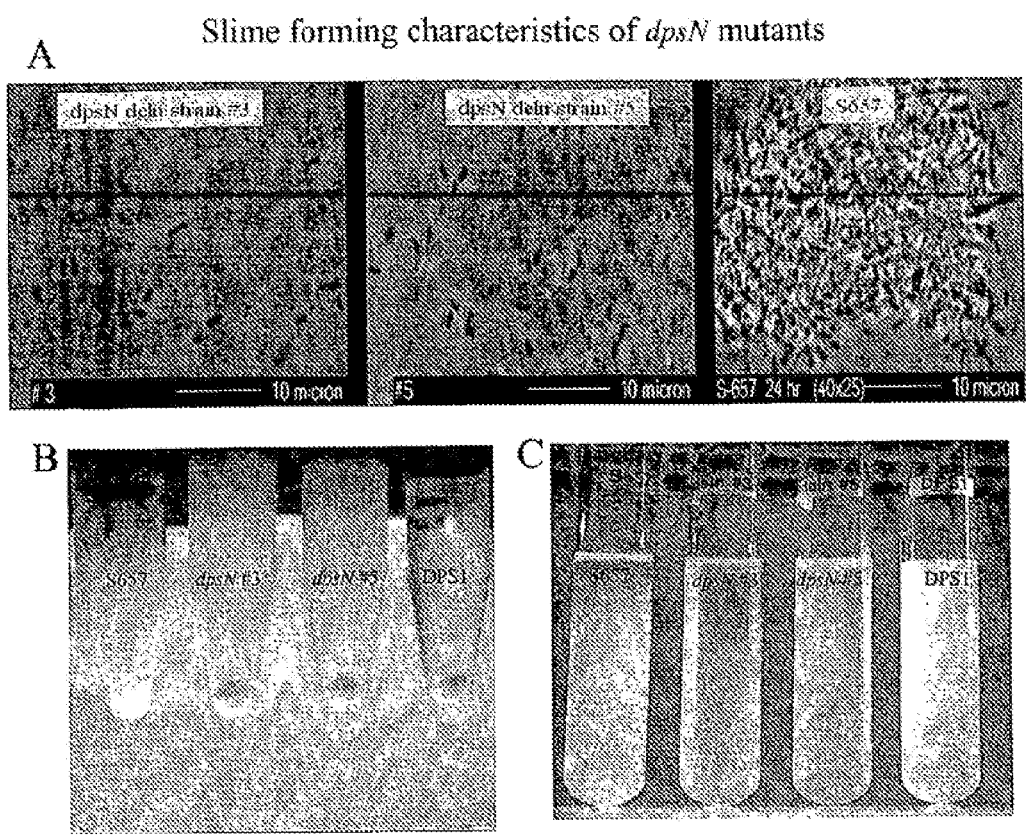
FIG. 5A-5C. Slime forming characteristics of dpsN mutants
Figure 6:
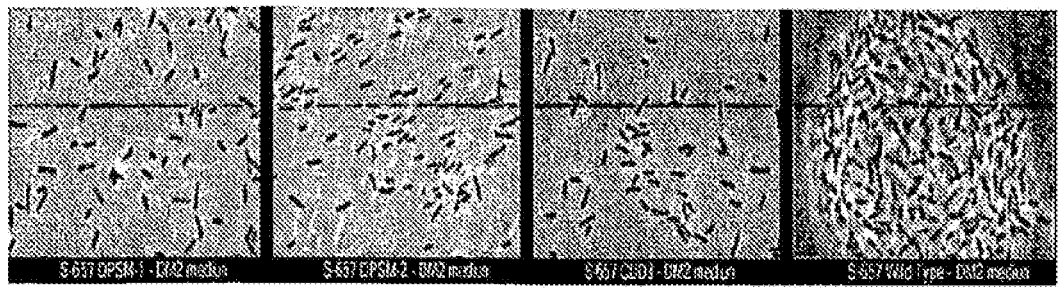
FIG. 6A-6B. Slime forming characteristics of dpsM mutants
Figure 6:

1. Microscopic evaluation of two dpsN deletion mutants (#3 and #5) and two dpsM deletion mutants (#1 and #5) grown about 16 hours in high carbon fermentation medium indicated that cells from these mutants did not form the large cell aggregates characteristic of the *Sphingomonas* capsular strain, S-657 (FIG. 5A, and FIG. 6A).

2. Wild-type ATCC 53159 cells grown in defined medium (DM2) with 1% glucose for 24 hours and diluted ten-fold formed visible clumps, where as the dpsM and dpsN slime mutants form uniform suspensions similar to that of a non-mucoid strain, DPS1 (FIG. 5C for dpsN).

3. Centrifugation of 24-hour cultures grown in DM2 medium with 1% glucose showed that the cells from the dpsM and dpsN slime mutants could be pelleted, whereas those from wild-type ATCC 53159 (S-657) remained attached to the polysaccharide, and thus did not pellet (FIG. 5B and FIG. 6B).

Six independent isolates of dpsN deletion mutants exhibited an average 5.4% increase in total precipitable material compared to the wild-type control, in shake flask fermentations. Selected dpsN and dpsM mutant isolates were evaluated in 20 L Applikon fermentors using media containing organic and inorganic nitrogen, salts and different carbon concentrations (3-5%). Polysaccharide was precipitated with isopropyl alcohol, dried and weighed. The dpsN mutants consistently exhibited a slight increase in total precipitable material compared to the wild-type capsular control strain. The dpsM mutants gave more variable and generally lower productivity as shown in Table 6.

TABLE 6

Increase in yield of polysaccharide with dps mutants

| | 5% carbon source | |
|---|---|---|
| dpsN #3 | n = 3 | 5.9% |
| dpsN #5 | n = 2 | 3.9% |
| dpsM #1 | n = 1 | −30.2% |
| dpsM #5 | n = 1 | 9.3% |
| | 3% carbon source | |
| dpsN #3 | n = 2 | 4.2% |
| dpsM #1 | n = 2 | −10.1% |
| dpsM #5 | n = 4 | −2.7% |

Example 11

Characterization of Diutan Slime-Form Polysaccharide

Rheological properties of diutan recovered from these fermentations by precipitation with isopropyl alcohol was determined, as shown in Table 7. Both dpsM and dpsN slime mutations resulted in improved viscosity of diutan.

TABLE 7

Rheological properties of diutan from slime mutants

| Strain | | SWV3 | % increase | 0.06 s−1, viscosity | % increase | LSRV | % Increase |
|---|---|---|---|---|---|---|---|
| wild-type | n = 5 | 26.7 | | 27,760 | | 2010 | |
| dpsN #3 | n = 5 | 35.3 | 32% | 37,920 | 37% | 3873 | 93% |
| dpsN #5 | n = 2 | 37.3 | 40% | 41,400 | 49% | 4075 | 103% |
| dpsM #1 | n = 3 | 40.5 | 52% | 37,733 | 36% | 3905 | 94% |
| dpsM #5 | n = 5 | 39.1 | 46% | 39440 | 42% | 3720 | 85% |
| | aver. | 42% | | aver. | 41% | aver. | 94% |

It was also observed that fiber quality, e.g., length, was improved with the slime mutants. Since the polysaccharide molecules are free in solution rather than attached to the surface of the cell, the precipitation of these molecules may be facilitated.

Low Shear Rate Viscosity Measurement.

Low shear rate viscosity is the viscosity of a 0.25% solution of diutan at 3 rpm. Standard or synthetic tap water was prepared by dissolving 10 g of NaCl and 1.47 g of $CaCl_2.2H_2O$ in 10 liters of deionized water. 4.5 g of Polyethylene Glycol (PEG) 200 was weighed directly in a 400-ml tall form beaker. A 0.75 g aliquot of diutan product was weighed, and dispersed in the PEG 200 to form a consistent slurry. 299 ml of synthetic tap water was added to the beaker and the mixture stirred at 800±20 rpm for approximately 4 hours. The beaker was removed from the stirring bench and placed in a 25° C. water bath and allowed to stand for 30 min. The viscosity was measured using a Brookfield LV Viscometer with the No. 2 spindle at 3 rpm.

Seawater Viscosity Measurement.

Seawater viscosity was determined using the following procedure. Seawater solution was prepared by dissolving 41.95 g of sea salt (ASTM D-1141-52, from Lake Products Co., Inc. Maryland Heights, Mo.) per 980 g deionized water, with pH adjusted to 8.2 with HCl or NaOH as needed. 307 g of seawater solution was transferred to a mixing cup; 0.86 g of diutan product was slowly added over 15-30 seconds to the mixing cup and allowed to mix at 11,500 rpm for 45 minutes in the Fann Multi-Mixer, Model 9B5 (Fann Instruments, Inc, Houston, Tex.). Three drops of Bara Defoam (NL Baroid/NL Industries, Inc., Houston, Tex.) was added and stirring was continued for an additional 30 seconds. The mixing cup was removed from the mixer and immersed in chilled water to lower the fluid's temperature, then placed in a constant temperature bath at 25° C. The solution was transferred to a 400-ml tall form beaker.

Fann viscosity (Fann Viscometer, Model 35A) was measured while mixing at low speed (3 rpm). The shear stress value was read from the dial and recorded as the SWv value at 3 rPm.

The viscosity was also determined on the Brookfield LV DV-II or DV-II viscometer with the LV-2C spindle. The 0.06 $sec^{-1}$ reading was measured at 0.3 rpm.

Example 12

Materials and Methods

Medium. YM contains per liter, 3 g yeast extract, 5 g peptone, 3 g malt extract, and 10 g glucose. DM2 medium contains per liter, 2.68 g $K_2HPO_4$, 1.31 g $KH_2PO_4$, 2.0 g $NH_4SO_4$, 0.1 g $MgSO_4.7H_2O$, 15 mg $CaCl_2.2H_2O$, 8.34 mg $FeSO_4.7H_2O$, 0.05 mg $MnCl_2.4H_2O$, 0.03 mg $CoCl_2.6H_2O$, 0.8 mg $CuSO_4.5H_2O$, 0.02 mg $Na_2MoO_4.2H_2O$, 1.0 mg $ZnSO_4.7H_2O$, 0.2 mg $H_3BO_3$ and 10 g glucose. Gellan shake flask fermentation medium contains per liter, 0.23 g NaCl, 0.165 g $CaCl_2.2H_2O$, 2.8 g $K_2HPO_4$, 1.2 g $KH_2PO_4$, 1.9 g $NaNO_3$, 1.0 g N—Z-Amine type EKC (Sheffield Products), 36.46 g Star-Dri corn syrup, 2.5 mg $FeSO_4.7H_2O$, 24 μg $CoCl_2.6H_2O$ and 0.1 g $MgSO_4.7H_2O$.

Centrifugation test for slime. Strains were grown approximately 24 hours at 30° C. in DM2 medium containing 1% glucose, with shaking at 350 rpm and then centrifuged at maximum speed (10,000 rpm) for 5 minutes in the Eppendorf centrifuge.

Hot settling test. Strains were grown in gellan shake flask fermentation medium. Fermentation broth was heated in the autoclave for 10 minutes to liquefy gellan. The hot broth was then transferred to a large test tube and allowed to settle overnight at 95° C. (to maintain broth as liquid). With a capsular strain the cells are attached to the polysaccharide and remain suspended. For slime-formers, the cells are not attached and precipitate during overnight incubation.

PCR amplification. The high fidelity PCR enzyme "PfuUltra hot start DNA polymerase" from Stratagene (LaJolla, Calif.) was used.

REFERENCES

The disclosure of each reference cited is expressly incorporated herein.
1. Coleman R C. 2001. Cloning and analysis of *Sphingomonas* sp. ATCC 53159 polysaccharide genes. San Diego State University MS thesis
2. Ditta G, S Stanfield, D Corbin and D R Helinski. 1980. Broad host range DNA cloning system for Gram-negative bacteria: construction of a gene bank of *Rhizobium meliloti*. Proc Natl Acad Sci USA 77: 7347-7351.
3. Harding N E, Y N Patel and R J. Coleman. 2004. Organization of genes required for gellan polysaccharide biosynthesis in *Sphingomonas elodea* ATCC 31461. J Ind Microbiol Biotechnol 31:70-82.
4. Lenz, O., E. Schwartz, J. Demedde, M. Eltinger and B. Friedrich. 1994. The *Alcaligenes eutrophus* H116 hoxX gene participates in hydrogenase regulation. J. Bacteriol. 176:4385-4393.
5. Matthews T D. 2004. Identification of genes involved in phenotypic phase shifting of *Sphingomonas* sp. ATCC 53159 San Diego State University MS thesis
6. Pollock T J and R W Armentrout. 1999. Planktonic/sessile dimorphism of polysaccharide-encapsulated Sphingomonads. J Ind Microbiol Biotechnol 23: 436-441.
7. Pollock, T J, W A T van Workum, L Thome, M Mikolajczak, M Yamazaki, J W Kijne and R W Armentrout. 1998. Assignment of biochemical functions to glycosyl transferase genes which are essential for biosynthesis of exopolysaccharides in *Sphingomonas* strain S88 and *Rhizobium leguminosarum*. J Bacteriol 180: 586-593.
8. Sa-Correia I, A M Fialho, P Videira, L M Moreira, A R Marques and H Albano. 2002. Gellan gum biosynthesis in *Sphingomonas paucimobilis* ATCC 31461: Genes, enzymes and exopolysaccharide production engineering. J Ind Microbiol Biotechnol. 29: 170-176.
9. Yamazaki M, L Thome, M Mikolajczak, R W Armentrout and T J. Pollock. 1996. Linkage of genes essential for synthesis of a polysaccharide capsule in *Sphingomonas* strain S88. J Bacteriol 178: 2676-2687.
10. U.S. Pat. No. 6,605,461.
11. U.S. Pat. No. 7,361,754.
12. U.S. Pat. No. 5,854,034.

The invention claimed is:

1. An isolated slime forming mutant *Sphingomonas* strain comprising a substitution, insertion or deletion in gene dpsN in a diutan biosynthetic gene cluster that inactivates gene dpsN and favors the production of a slime form polysaccharide, wherein said dpsN comprises the nucleotide sequence of nucleotides 1321-2019 as set forth in SEQ ID NO:14.

2. The isolated slime forming mutant *Sphingomonas* strain of claim 1, wherein said slime forming mutant *Sphingomonas* strain produces diutan.

3. The isolated slime forming mutant *Sphingomonas* strain of claim 2, wherein said diutan is a slime form polysaccharide.

4. The isolated slime forming mutant *Sphingomonas* strain of claim 3, wherein said diutan comprises longer fibers than diutan as naturally produced by a wild-type strain ATCC 53159.

5. The isolated slime forming mutant *Sphingomonas* strain of claim 3, wherein said diutan imparts to a fluid an increased viscosity relative to an equivalent amount of diutan as naturally produced by a wild-type *Sphingomonas* strain ATCC 53159.

6. The isolated slime forming mutant *Sphingomonas* strain of claim 5, wherein the increased viscosity is at least 30% more than an equivalent amount of diutan produced by the wild-type strain ATCC 53159.

7. The isolated slime forming mutant *Sphingomonas* strain of claim 5, wherein the increased viscosity is at least 50% more than an equivalent amount of diutan produced by the wild-type strain ATCC 53159.

8. The isolated slime forming mutant *Sphingomonas* strain of claim 5, wherein the increased viscosity is at least 80% more than an equivalent amount of diutan produced by the wild-type strain ATCC 53159.

9. The isolated slime forming mutant *Sphingomonas* strain of claim 5, wherein the increased viscosity is at least 90% more than an equivalent amount of diutan produced by the wild-type strain ATCC 53159.

10. The isolated slime forming mutant *Sphingomonas* strain of claim 1, further comprising a second gene mutation, insertion or deletion in gene I (dpsI) comprising a nucleotide sequence of 501-1472 as set forth in SEQ ID NO:29, in gene R (dpsR) comprising a nucleotide sequence of 501-2498 as set forth in SEQ ID NO:31, or in gene M (dpsM) comprising a nucleotide sequence of 456-1337 as set forth in SEQ ID NO:14.

11. The isolated slime forming mutant *Sphingomonas* strain of claim 1, wherein said mutant *Sphingomonas* strain is a variant of a wild-type *Sphingomonas* strain ATCC 53159, wherein said variant has been genetically engineered to eliminate an expression of said dpsN.

* * * * *

SEQUENCE LISTING

<160> NUMBER OF SEQ ID NOS: 32

<210> SEQ ID NO 1
<211> LENGTH: 26
<212> TYPE: DNA
<213> ORGANISM: Sphingomonas elodea

<400> SEQUENCE: 1
tggagctcgg tgctgtggtt gttctt                                   26

<210> SEQ ID NO 2
<211> LENGTH: 26
<212> TYPE: DNA
<213> ORGANISM: Sphingomonas elodea -continued

<400> SEQUENCE: 2
ggtctagagt cacgccggtt gaacat                                          26

<210> SEQ ID NO 3
<211> LENGTH: 26
<212> TYPE: DNA
<213> ORGANISM: Sphingomonas elodea

<400> SEQUENCE: 3
agtctagagc ctgaacgccg aaaggg                                          26

<210> SEQ ID NO 4
<211> LENGTH: 27
<212> TYPE: DNA
<213> ORGANISM: Sphingomonas elodea

<400> SEQUENCE: 4
gttgcatgcg gtgatggtgg agaatgg                                         27

<210> SEQ ID NO 5
<211> LENGTH: 26
<212> TYPE: DNA
<213> ORGANISM: Sphingomonas sp.

<400> SEQUENCE: 5
ttgagctcgc tgtggctgtt cttcct                                          26

<210> SEQ ID NO 6
<211> LENGTH: 26
<212> TYPE: DNA
<213> ORGANISM: Sphingomonas sp.

<400> SEQUENCE: 6
cgtctagagt cacgccggtt gaacat                                          26

<210> SEQ ID NO 7
<211> LENGTH: 27
<212> TYPE: DNA
<213> ORGANISM: Sphingomonas sp.

<400> SEQUENCE: 7
tctctagact cggtcaccag gtctgaa                                         27

<210> SEQ ID NO 8
<211> LENGTH: 23
<212> TYPE: DNA
<213> ORGANISM: Sphingomonas sp.

<400> SEQUENCE: 8
ctcgcatgcc ggtaaaggtg aag                                             23

<210> SEQ ID NO 9
<211> LENGTH: 26
<212> TYPE: DNA
<213> ORGANISM: Sphingomonas sp.

<400> SEQUENCE: 9
ttgagctcga tcggcgttaa gactgc                                          26

<210> SEQ ID NO 10
<211> LENGTH: 27
<212> TYPE: DNA
<213> ORGANISM: Sphingomonas sp.

-continued

<400> SEQUENCE: 10
cgtctagatc atcgcggtcg ctgccat                                          27

<210> SEQ ID NO 11
<211> LENGTH: 27
<212> TYPE: DNA
<213> ORGANISM: Sphingomonas sp.

<400> SEQUENCE: 11
cctctagacg tcggaggcat catgttc                                          27

<210> SEQ ID NO 12
<211> LENGTH: 26
<212> TYPE: DNA
<213> ORGANISM: Sphingomonas sp.

<400> SEQUENCE: 12
tcgcatgctc tgctgattgc cgttct                                           26

<210> SEQ ID NO 13
<211> LENGTH: 2459
<212> TYPE: DNA
<213> ORGANISM: Sphingomonas elodea

<400> SEQUENCE: 13
gggctgcagc ttcacggcgg tgaacctcgc cacggcgctg cccagatcg gcatcaagac       60
cgcgctggtc gatgcgaacc tgcgcgattc aagcatcggc gcagctttcg gcatcgcgtc    120
ggacaagctg ggtcttgccg actatctcgg caagggcgat gtcgacctcg cctcaatcct    180
ccacccgacc agcctcgacc agctctttat tatccccgcc ggtcatgtcg agcacagccc    240
gcaggaactg ctttcgtccg aacagttcca cgacctggcg acccagctgc agcgcgagtt    300
cgacatcacg atcttcgaca ccaccgccgc caacacctgt gccgatgcac agcgcgtggc    360
ccaggtggcc ggctacgccc tgatcgtcgg tcgcaaggac gccagctaca tgcgcgacgt    420
caccacgctc agccgcacgc tgcgcgcgga ccggaccaac gtcatcggct gcgtgctgaa    480
cggctactga cttggatcag atgaccgcaa ccgcgcaggc gcggcggcag gcaggcaag    540
gcggcggctt ctggcttgcc gtcgccgggc tcgcctccct tgccattccc accttcgtga    600
cgctcggccg ccaggtctgg agcgcggagg gcggcgtgca gggaccgatc gtcctcgcca    660
ccggcgcctg gatgcttgcc cgccagcgcg gcaccatcga ggcgctgcgc agccggggca    720
acctgttctt gggcggtctc gcgctcttgc tggccctgtg catctacacc ggcggccgcg    780
tgttcgactt ctcgagcatc gaaacactgg gcctggtcgc cacccggtc gccgccggct    840
ttctctattt cggagggcgc gcgatccggg ccacctggtt cccggtgctg tggttgttct    900
tcctcgtgcc gccaccgggc tgggcggtcg atcgcgtgac cgcgccgctc aaggaattcg    960
tgtcctacgc ggcaaccggc ctgctttcgc gcttcgacta tccgatcctg cgcgagggcg   1020
tgacgctcta tgtcggcccc tatcagctgc tcgttgagga cgcctgctcg ggccttcgat   1080
cgctgtcgag ccttgtcgtc gtcacgctgc tgtacatcta catcaagaac aagccgtcct   1140
ggcgctatgc gctgttcatc gccgcgctgg tgatcccggt ggcggtgttc accaatgtat   1200
tgcgcatcat catcctcgtg ctgatcacct accatatggg tgacgaggcg gcgcagagct   1260
tcctccacgt ttccaccggc atggtgatgt tcgtggtggc cctgctgtgc atcttcgcga   1320
tcgactgggt ggtcgagcag cttctcctcg tacgtcggag gcatcatgtt caaccggcgt   1380
gacctgctga tcggcgcggg ctgcttcgcc gctgccggcg cctcgctcgg cctgaagccg   1440

```
catcgccgca tggacctgct cggcgatacc aagctcgacg cgctgatgcc caaggccttt   1500
ggcgcgtgga aggcggagga taccggctcg ctgatcgcgc cggcccgcga gggcagcctg   1560
gaggacaagc tgtacaacca ggtcgtcagc cgcgcctttt cgcgtccgga cggcacccag   1620
gtgatggtgc tgattgccta tggcaacgcc cagaccgatc tgctgcagct gcaccgcccg   1680
gaagtctgct acccgttctt cggcttcacc gtcgaggaaa gccatgcgca gtcgattccg   1740 gtgaccccccc aggtgaccat tcccggccgg gcgatgaccg cgagcaactt caaccgtacc   1800
gagcagatcc tctactgggc gcgcgtcggc gagtttctgc cccagagcgg caacgagcag   1860
ctgctcgccc gcctgaagag ccaggtgcag ggctggatcg tcgacggtgt gctggtgcgt   1920
atctccaccg tgacgaccga tgcggccgag gggctcgagg ccaatctcga tttcgcccgc   1980
gagctggtca agacgctcga tccgcgggtg cagcgtccgt tgctcggcac gaacctgacg   2040
cggcggctcg ccgagcgcgc ctgaacgccg aaaggggcgg cagccggtac cgccccttcc   2100
ctctccaccg caccggagcg gtatttcagc gttcgtggag cgcgtcgctt ccggtctcga   2160
gcatcgggcc gaccagatag ctgagcaggg tgcgcttgcc ggtcacgata tcggcgctgg   2220
cgaccatgcc gggccgcagc ggcacgcgcg ccccgttggc gaggatatag ccgcggtcga   2280
gcgcgattcg cgccttgtag accggcggct gaccgtcccg cacctgcacc gcctccgggc   2340
tgatcccgac caccgtcccg ggaatcatgc catagcgggt ataggggaag gcctgcagct   2400
tcacctttac cggcatcccg gtccggacga agccgatatc gccattctcc accatcacc    2459

<210> SEQ ID NO 14
<211> LENGTH: 2403
<212> TYPE: DNA
<213> ORGANISM: Sphingomonas sp.

<400> SEQUENCE: 14
gatcggcgtt aagactgcgc tggtcgatgc caatctgcgc gatcccagca tcggcgcagc     60
cttcggcctc gccgccgaca agcccggcct ggccgattat ctcgcctcgg gcgatgtcga    120
cctcgcctcg atcatccatg cgacccgcct cgaccagctc tcgatcatcc cggccgggca    180
tgtcgagcac agcccgcagg aactgctcgc gtccgaacag ttccatgatc tggcgacgca    240
gctgctgcgc gagttcgaca tcacgatctt cgacaccacg cgtccaaca cctgcgccga    300 cgcgcagcgt gtcgcgcata tcgccggcta tgcgatcatc gtggcgcgca aggatgcgag    360
ctacatccgc gacgtgaaca cgctcagccg cacgctgcgt gcagaccgca ccaacgtcat    420
cggctgcgta ctgaacggct attgatttgg accatatggc agcgaccgcg atgacgcggc    480
agcaggagag gaagggcggt ggctattggc tggccgttgc cggtcttgcc gcgctaacca    540
tcccgacctt catcaccctg ggtcgcgagg tttggagtgc ggaaggcggc gtgcagggtc    600
cgatcgtgct cgccacgggc gcctggatgc tggcccgcca gtgctcgacg atcgaggcgc    660
tacgccgccc cggcagcgtg ctgctcggcg cgctgttcct gctggcgacg cttgccttct    720
acaccgttgg acgggtgttc gacttcatca gtgtcgaaac cttcggactg gtcgcgacct    780
atctggtcgt cgcctatctc tatttcggtg ccagggtgct ccgtgccgcc tggttcccgg    840
tgctgtggct gttcttcctg gtgccgccgc ccggctgggc cgtcgaccgc atcaccgcac    900
cgctcaagga gttcgtctcc tatgcggcaa cgggcctgct ttcctgggtg gattatccga    960
tcctgcgcca gggcgtgaca ctgttcgtcg gcccctatca gctgctcgtc gaagatgcct   1020
gttcgggtct gcgctcgctg tccagcctgg tcgtcgtgac gctgctctac atctacatca   1080
agaacaagcc gtcctggcgc tacgcggcgt tcatcgcagc gctggtgatc ccggtggcag   1140
```

```
tggtgaccaa cgtcctgcgg atcatcatcc tggtactgat cacctatcat ctgggcgacg    1200
aggcggcgca gagcttcctc cacgtctcca ccggcatggt gatgttcgtg gtcgccctgc    1260
tttgcatctt cgcgatcgac tgggtggtcg agcaacttct tctcctgcgt cggaggcatc    1320
atgttcaacc ggcgtgacct gctgatcggc gcaggctgct tcgccgccgc tggcgcctcg    1380
ctcggcctga agccgcaccg gcggatggac ctgctgggcg acaccaagct cgacacgctg    1440
atgcccaagg cattcggcgc atggaaggca gaggataccg gttcgctgat cgcgccggcg    1500
cgcgaaggca gcctggagga caagctctac aaccaggtgg tcacccgcgc cttctcccgc    1560
gcggacggtg cccaagtgat gctgctgatc gcctatggca acgcccagac cgatctactg    1620
cagctgcacc ggccgaaaat atgctacccg ttcttcggct tcaccgtggt ggaaagccat    1680
gagcagacca tcccggtgac gccgcaggtg acgatccccg tcgcgcgcct gaccgccacc    1740
aacttcaacc gcaccgagca gatcctctac tggacccgcg tcggcgaata tctgccgcag    1800
aacggcaatc agcagatgct cgcgcggctg aagagccagg tccagggctg gatcgtcgac    1860
ggtgtgctgg tgcgcatctc gacggtgacg cccgaggcgg aagatggcct gagcgccaat    1920
ctcgatttcg cgcgcgagct ggtgaagacg ctcgacccgc gcgtgctgcg cccgctgctc    1980
gggaacgggc tcacacggca gctcggtcac caggtctgaa ccggtgcgcc gcacgcggcg    2040
cccccggcaa caaaaaagga gcggcgcggg ccgccgccgc tccctctcct tctcatgcgg    2100
cgccctgccc tcaccgctcg tgcagcgcgt cactccccgt ctcgagcacg ggccccacca    2160
gatagctgaa cagggttcgc ttgccggtga cgatgtccgc gctcgcgagc atccccggcc    2220
gcagcggcac ctgtgcgcca tgggccagca catacccgcg cgccagcgcg atccgcgcct    2280
tgtagaccgg cggctggttc tccttcatct gcaccgcctc ggggctgatg cccgccaccg    2340
tgccgggaat catgccgtag cgggtatagg gaaaggcctg cagcttcacc tttaccggca    2400
tgc                                                                  2403
```

<210> SEQ ID NO 15
<211> LENGTH: 232
<212> TYPE: PRT
<213> ORGANISM: Sphingomonas elodea

<400> SEQUENCE: 15

```
Met Phe Asn Arg Arg Asp Leu Leu Ile Gly Ala Gly Cys Phe Ala Ala
1               5                   10                  15

Ala Gly Ala Ser Leu Gly Leu Lys Pro His Arg Arg Met Asp Leu Leu
            20                  25                  30

Gly Asp Thr Lys Leu Asp Ala Leu Met Pro Lys Ala Phe Gly Ala Trp
        35                  40                  45

Lys Ala Glu Asp Thr Gly Ser Leu Ile Ala Pro Ala Arg Glu Gly Ser
    50                  55                  60

Leu Glu Asp Lys Leu Tyr Asn Gln Val Val Ser Arg Ala Phe Ser Arg
65                  70                  75                  80

Pro Asp Gly Thr Gln Val Met Val Leu Ile Ala Tyr Gly Asn Ala Gln
                85                  90                  95

Thr Asp Leu Leu Gln Leu His Arg Pro Glu Val Cys Tyr Pro Phe Phe
            100                 105                 110

Gly Phe Thr Val Glu Glu Ser His Ala Gln Ser Ile Pro Val Thr Pro
        115                 120                 125

Gln Val Thr Ile Pro Gly Arg Ala Met Thr Ala Ser Asn Phe Asn Arg
    130                 135                 140
```

```
Thr Glu Gln Ile Leu Tyr Trp Ala Arg Val Gly Glu Phe Leu Pro Gln
145                 150                 155                 160

Ser Gly Asn Glu Gln Leu Leu Ala Arg Leu Lys Ser Gln Val Gln Gly
                165                 170                 175

Trp Ile Val Asp Gly Val Leu Val Arg Ile Ser Thr Val Thr Thr Asp
            180                 185                 190

Ala Ala Glu Gly Leu Glu Ala Asn Leu Asp Phe Ala Arg Glu Leu Val
        195                 200                 205

Lys Thr Leu Asp Pro Arg Val Gln Arg Pro Leu Leu Gly Thr Asn Leu
210                 215                 220

Thr Arg Arg Leu Ala Glu Arg Ala
225                 230

<210> SEQ ID NO 16
<211> LENGTH: 293
<212> TYPE: PRT
<213> ORGANISM: Sphingomonas elodea

<400> SEQUENCE: 16

Met Thr Ala Thr Ala Gln Ala Arg Arg Gln Gly Arg Gln Gly Gly Gly
1               5                   10                  15

Phe Trp Leu Ala Val Ala Gly Leu Ala Ser Leu Ala Ile Pro Thr Phe
            20                  25                  30

Val Thr Leu Gly Arg Gln Val Trp Ser Ala Glu Gly Gly Val Gln Gly
        35                  40                  45

Pro Ile Val Leu Ala Thr Gly Ala Trp Met Leu Ala Arg Gln Arg Gly
    50                  55                  60

Thr Ile Glu Ala Leu Arg Gln Pro Gly Asn Leu Phe Leu Gly Gly Leu
65                  70                  75                  80

Ala Leu Leu Leu Ala Leu Cys Ile Tyr Thr Gly Gly Arg Val Phe Asp
                85                  90                  95

Phe Ser Ser Ile Glu Thr Leu Gly Leu Val Ala Thr Leu Val Ala Ala
            100                 105                 110

Gly Phe Leu Tyr Phe Gly Gly Arg Ala Ile Arg Ala Thr Trp Phe Pro
        115                 120                 125

Val Leu Trp Leu Phe Phe Leu Val Pro Pro Gly Trp Ala Val Asp
130                 135                 140

Arg Val Thr Ala Pro Leu Lys Glu Phe Val Ser Tyr Ala Ala Thr Gly
145                 150                 155                 160

Leu Leu Ser Arg Phe Asp Tyr Pro Ile Leu Arg Glu Gly Val Thr Leu
                165                 170                 175

Tyr Val Gly Pro Tyr Gln Leu Leu Val Glu Asp Ala Cys Ser Gly Leu
            180                 185                 190

Arg Ser Leu Ser Ser Leu Val Val Thr Leu Leu Tyr Ile Tyr Ile
        195                 200                 205

Lys Asn Lys Pro Ser Trp Arg Tyr Ala Leu Phe Ile Ala Ala Leu Val
    210                 215                 220

Ile Pro Val Ala Val Phe Thr Asn Val Leu Arg Ile Ile Leu Val
225                 230                 235                 240

Leu Ile Thr Tyr His Met Gly Asp Glu Ala Ala Gln Ser Phe Leu His
                245                 250                 255

Val Ser Thr Gly Met Val Met Phe Val Ala Leu Leu Cys Ile Phe
            260                 265                 270

Ala Ile Asp Trp Val Val Glu Gln Leu Leu Leu Val Arg Arg Arg His
        275                 280                 285
```

His Val Gln Pro Ala
            290

<210> SEQ ID NO 17
<211> LENGTH: 232
<212> TYPE: PRT
<213> ORGANISM: Sphingomonas sp.

<400> SEQUENCE: 17

Met Phe Asn Arg Arg Asp Leu Leu Ile Gly Ala Gly Cys Phe Ala Ala
1               5                   10                  15

Ala Gly Ala Ser Leu Gly Leu Lys Pro His Arg Arg Met Asp Leu Leu
            20                  25                  30

Gly Gly Thr Lys Leu Asp Thr Leu Met Pro Lys Ala Phe Gly Ala Trp
        35                  40                  45

Lys Ala Glu Asp Thr Gly Ser Leu Ile Ala Pro Ala Arg Glu Gly Ser
    50                  55                  60

Leu Glu Asp Lys Leu Tyr Asn Gln Val Val Thr Arg Ala Phe Ser Arg
65                  70                  75                  80

Ala Asp Gly Ala Gln Val Met Leu Leu Ile Ala Tyr Gly Asn Ala Gln
                85                  90                  95

Thr Asp Leu Leu Gln Leu His Arg Pro Glu Ile Cys Tyr Pro Phe Phe
            100                 105                 110

Gly Phe Thr Val Val Glu Ser His Glu Gln Thr Ile Pro Val Thr Pro
        115                 120                 125

Gln Val Thr Ile Pro Gly Arg Ala Leu Thr Ala Thr Asn Phe Asn Arg
    130                 135                 140

Thr Glu Gln Ile Leu Tyr Trp Thr Arg Val Gly Glu Tyr Leu Pro Gln
145                 150                 155                 160

Asn Gly Asn Gln Gln Met Leu Ala Arg Leu Lys Ser Gln Val Gln Gly
                165                 170                 175

Trp Ile Val Asp Gly Val Leu Val Arg Ile Ser Thr Val Thr Pro Glu
            180                 185                 190

Ala Glu Asp Gly Leu Ser Ala Asn Leu Asp Phe Ala Arg Glu Leu Val
        195                 200                 205

Lys Thr Leu Asp Pro Arg Val Leu Arg Pro Leu Leu Gly Asn Gly Leu
    210                 215                 220

Thr Arg Gln Leu Gly His Gln Val
225                 230

<210> SEQ ID NO 18
<211> LENGTH: 293
<212> TYPE: PRT
<213> ORGANISM: Sphingomonas sp.

<400> SEQUENCE: 18

Met Ala Ala Thr Ala Met Thr Arg Gln Gln Glu Arg Lys Gly Gly Gly
1               5                   10                  15

Tyr Trp Leu Ala Val Ala Gly Leu Ala Ala Leu Thr Ile Pro Thr Phe
            20                  25                  30

Ile Thr Leu Gly Arg Glu Val Trp Ser Ala Glu Gly Val Gln Gly
        35                  40                  45

Pro Ile Val Leu Ala Thr Gly Ala Trp Met Leu Ala Arg Gln Cys Ser
    50                  55                  60

Thr Ile Glu Ala Leu Arg Arg Pro Gly Ser Val Leu Leu Gly Ala Leu
65                  70                  75                  80

Phe Leu Leu Ala Thr Leu Ala Phe Tyr Thr Val Gly Arg Val Phe Asp

```
                    85                  90                  95
Phe Ile Ser Val Glu Thr Phe Gly Leu Val Ala Thr Tyr Leu Val Val
            100                 105                 110
Ala Tyr Leu Tyr Phe Gly Ala Arg Val Leu Arg Ala Ala Trp Phe Pro
        115                 120                 125
Val Leu Trp Leu Phe Phe Leu Val Pro Pro Gly Trp Ala Val Asp
    130                 135                 140
Arg Ile Thr Ala Pro Leu Lys Glu Phe Val Ser Tyr Ala Thr Gly
145                 150                 155                 160
Leu Leu Ser Trp Val Asp Tyr Pro Ile Leu Arg Gln Gly Val Thr Leu
                165                 170                 175
Phe Val Gly Pro Tyr Gln Leu Leu Val Glu Asp Ala Cys Ser Gly Leu
            180                 185                 190
Arg Ser Leu Ser Ser Leu Val Val Thr Leu Leu Tyr Ile Tyr Ile
        195                 200                 205
Lys Asn Lys Pro Ser Trp Arg Tyr Ala Ala Phe Ile Ala Ala Leu Val
    210                 215                 220
Ile Pro Val Ala Val Thr Asn Val Leu Arg Ile Ile Leu Val
225                 230                 235                 240
Leu Ile Thr Tyr His Leu Gly Asp Glu Ala Ala Gln Ser Phe Leu His
                245                 250                 255
Val Ser Thr Gly Met Val Met Phe Val Ala Leu Leu Cys Ile Phe
            260                 265                 270
Ala Ile Asp Trp Val Val Glu Gln Leu Leu Leu Leu Arg Arg Arg His
        275                 280                 285
His Val Gln Pro Ala
    290

<210> SEQ ID NO 19
<211> LENGTH: 42
<212> TYPE: DNA
<213> ORGANISM: Sphingomonas sp.
<220> FEATURE:
<221> NAME/KEY: CDS
<222> LOCATION: (1)...(42)

<400> SEQUENCE: 19 atg ttc aac cgg cgt gac tct aga ctc ggt cac cag gtc tga          42
Met Phe Asn Arg Arg Asp Ser Arg Leu Gly His Gln Val  *
1               5                   10

<210> SEQ ID NO 20
<211> LENGTH: 13
<212> TYPE: PRT
<213> ORGANISM: Sphingomonas sp.

<400> SEQUENCE: 20

Met Phe Asn Arg Arg Asp Ser Arg Leu Gly His Gln Val
1               5                   10

<210> SEQ ID NO 21
<211> LENGTH: 27
<212> TYPE: DNA
<213> ORGANISM: Sphingomonas elodea

<400> SEQUENCE: 21
acgagctcag atcagccgca acctcct                                    27

<210> SEQ ID NO 22
<211> LENGTH: 27
```

```
<212> TYPE: DNA
<213> ORGANISM: Sphingomonas elodea

<400> SEQUENCE: 22
gctctagacg ccggcatgtt aatcacc                                         27

<210> SEQ ID NO 23
<211> LENGTH: 27
<212> TYPE: DNA
<213> ORGANISM: Sphingomonas elodea

<400> SEQUENCE: 23
gctctagaga tgcgttccac gcctgac                                         27

<210> SEQ ID NO 24
<211> LENGTH: 27
<212> TYPE: DNA
<213> ORGANISM: Sphingomonas elodea

<400> SEQUENCE: 24
atgcatgccg atcgcgctca tcagggt                                         27

<210> SEQ ID NO 25
<211> LENGTH: 1903
<212> TYPE: DNA
<213> ORGANISM: Sphingomonas elodea
<220> FEATURE:
<221> NAME/KEY: gene
<222> LOCATION: (501)..(1403)

<400> SEQUENCE: 25
agcttggcga acagcgcggt gaaatagacc gcgccggcac ctgtcgagat tacgacgtcc     60
ggcttgtgcc tgcggacgat ggcgaggctc tgccgcaggt tgcgcagggc gccgccgagc    120
atcttgaagg ggtggcccag ccgggcctgg ccaagcgcat aatggccgac cagctccacc    180
ggatgtttct ccgcgagact gcggccaagg gccgtatctt cggtgacgaa gaagtaatcg    240
tgttcgcgcc agaccgactc cagatccagg atctgccgca gatggccccc gccggacgct    300
gcgaggcaca ttttcagtcg cttgcccgtc gtgtgcgccg cctcggtcgc ttctgccatg    360
ctgtccccct gccttcgcgg ctggcccccg gggcgggagc catgctgcac tgccaacgct    420
attgcggatg cccgcccgtc cgaataggtt caagtagaag tttgtgccgt gcgcaattcc    480
gtgccggcag ggaggtcttc atgaagaaat tgtacctggt aacggcagtg gccgcggccg    540
cgctcgccgt ctccggatgt ggcagcaagg aaggcaagct cgacaagggg caggttgtcg    600
ccaccgtcga tggcgatgag atcaccgttt tcgagctcaa tgccgaggtg caggccgcgc    660
cggtaccgca ggggaccgac cgcaagctgg ccgagcagct cgcgctgcag cgcatcatcg    720
aacgcaagat cctgtcgaag atcgcgcgtg agcagaagct cgacaagacg ccgtccttcc    780
tgatccagca gcgccgtgcg gacgagctga tcctcacgag catgctgcgc gacaagatcg    840
ccggcggcat cagccagccg accgatgccg atgtggcaca atatcaggcc gcgcatccgg    900
atcggttcgc ccagcgcaag gtctacagca tcgagcagat cgtgttcccg ccgcccagtt    960
cgtcggacaa gttcaaagag ttcgcgccac tcaagacgct ggaccagctc gccgccaagc   1020
tgactgccga cggcgtgcag ttccgccgcg cgcccaccca gctcgacacc gcagcacttc   1080
cgccggaaat cgccggcaag atcgcggcgt tgccggcggc ggaaatgttc atcctgccga   1140
cccagcaggg catcaccgcc aatgtgatca ccgcgaccac gatccagccg ctgaccggcg   1200
accaggcgcg cgaagtggcg ctgaacgcgc tgcgcaccga acgcttcagc aaggcagccg   1260
```

-continued

```
acgcccagct gaacgagcgg ctgaagaagg cgcgggaaac cgtgaagtac cagccgggct    1320
atggcgcgcc gccgcagctc aagggcggcg ctgcgcccaa ggccacgcct gcgcccgagg    1380
cgccgatgca gaacagccag taaatccagc ggggaggaag ttcgcttcct cccccacgga    1440
ttgcggggcg cgaagcccgc gatcacttct tggcgggata tcccgcccac cagcgccgcc    1500
gttcgcgcac gaccggcgcc caggcgcggc tgaccgcggt caggcgttcg cgcttcttcg    1560
gcaacagcgg cgccagcagg ctgccgagca gctgatattt cagcgcggcg agccagatcg    1620
cccagccggt gacgagcgcg ccgcccttgg tgaaatgctt gcgggcatag tgcatccgtc    1680
cggtcgtcat gaacatgata cggctggagg aaagggaatg gccgctgccg gcatcgtgga    1740
ccaccgcgac gccgggatcg accagtaccg cataaccgcg ttcgcggatg cgtttgaaca    1800
tgtcgacttc ctccgaatag aggaagaagc tctcgtcgaa gccgccgatc tcgcgccaga    1860
catcggcacg gaccatcatg aagccgccgt tgagcacgtc gac                      1903
```

<210> SEQ ID NO 26
<211> LENGTH: 300
<212> TYPE: PRT
<213> ORGANISM: Sphingomonas elodea

<400> SEQUENCE: 26

```
Met Lys Lys Leu Tyr Leu Val Thr Ala Val Ala Ala Ala Leu Ala
1               5                   10                  15

Val Ser Gly Cys Gly Ser Lys Glu Gly Lys Leu Asp Lys Gly Gln Val
                20                  25                  30

Val Ala Thr Val Asp Gly Asp Glu Ile Thr Val Phe Glu Leu Asn Ala
                35                  40                  45

Glu Val Gln Ala Ala Pro Val Pro Gln Gly Thr Asp Arg Lys Leu Ala
    50                  55                  60

Glu Gln Leu Ala Leu Gln Arg Ile Ile Glu Arg Lys Ile Leu Ser Lys
65                  70                  75                  80

Ile Ala Arg Glu Gln Lys Leu Asp Lys Thr Pro Ser Phe Leu Ile Gln
                85                  90                  95

Gln Arg Arg Ala Asp Glu Leu Ile Leu Thr Ser Met Leu Arg Asp Lys
            100                 105                 110

Ile Ala Gly Gly Ile Ser Gln Pro Thr Asp Ala Asp Val Ala Gln Tyr
        115                 120                 125

Gln Ala Ala His Pro Asp Arg Phe Ala Gln Arg Lys Val Tyr Ser Ile
    130                 135                 140

Glu Gln Ile Val Phe Pro Pro Ser Ser Ser Asp Lys Phe Lys Glu
145                 150                 155                 160

Phe Ala Pro Leu Lys Thr Leu Asp Gln Leu Ala Ala Lys Leu Thr Ala
                165                 170                 175

Asp Gly Val Gln Phe Arg Arg Ala Pro Thr Gln Leu Asp Thr Ala Ala
            180                 185                 190

Leu Pro Pro Glu Ile Ala Gly Lys Ile Ala Leu Pro Ala Ala Glu
        195                 200                 205

Met Phe Ile Leu Pro Thr Gln Gln Gly Ile Thr Ala Asn Val Ile Thr
    210                 215                 220

Ala Thr Thr Ile Gln Pro Leu Thr Gly Asp Gln Ala Arg Glu Val Ala
225                 230                 235                 240

Leu Asn Ala Leu Arg Thr Glu Arg Phe Ser Lys Ala Ala Asp Ala Gln
                245                 250                 255

Leu Asn Glu Arg Leu Lys Lys Ala Arg Glu Thr Val Lys Tyr Gln Pro
            260                 265                 270
```

-continued

Gly Tyr Gly Ala Pro Pro Gln Leu Lys Gly Gly Ala Ala Pro Lys Ala
       275                 280                 285

Thr Pro Ala Pro Glu Ala Pro Met Gln Asn Ser Gln
       290                 295             300

<210> SEQ ID NO 27
<211> LENGTH: 2858
<212> TYPE: DNA
<213> ORGANISM: Sphingomonas elodea

<400> SEQUENCE: 27

| | | | | | |
|---|---|---|---|---|---|
| agatcagccg | caacctcctc | gccgccggcc | tgtccggcgc | gacgccggtg | ctggtggcga | 60 |
| gcgacatcag | cctcgggacc | gagcgcctgc | tccgcacccg | gctggacctg | ctgccgctcg | 120 |
| ccgcgcgcgc | cattaccgag | gaccagccga | cgctgatcct | ggtcggcgat | gcggtggccg | 180 |
| gcggcgcgga | cagaccggcc | gcggtccgag | aatcggtcct | ccctgaatc | ctatgtcccg | 240 |
| cggaaggcgg | ggctggtcgt | gcgagacctg | tacgcccggc | ggtgggcgca | gccgccttgt | 300 |
| cgagcgcgcc | cgcggttggc | cccattgcct | ctcaagttgc | tgaaaacctg | cgcccgataa | 360 |
| taagcattaa | acgatccgaa | accatggagt | ttcaacgata | tttcatgcc | ttgtgtgaag | 420 |
| tttccgcatg | agggaatcac | gcgtcgattg | gggtcgacca | gtaacaaggt | gattaacatg | 480 |
| ccggcgatta | ccgttaaaaa | tcaggctgag | ttagacgcgg | ctatcaagac | ggccaagggc | 540 |
| ggcgacacga | tcctgcttgc | tcctggtacc | tattcgtcgg | tgacgatgac | gaatatcaag | 600 |
| ccggcaaccg | tgctgacgat | ccagtcgctc | gatacgaaga | acccggcggt | cgtgcagtcg | 660 |
| ctgtggatct | cgtcttcgaa | caacatcact | ttcaaggacc | tggacgtgaa | gcgggattac | 720 |
| aggcccgcga | acgactggga | aactgctagt | cggatcctga | attcgaacaa | tatcacagtg | 780 |
| gacaacgtcc | ggttcagcgg | cggcagcggc | gatcctgcat | tatcaaccgg | cgtcgggctc | 840 |
| agcatacgct | cgggcacgaa | catcaagttt | ctcaactcct | ccgtcgacca | ttttgggcta | 900 |
| ggactgagcg | tacaagacat | caacaaaatg | acggtgcagg | aagcacctt | tcgtgacaac | 960 |
| cggcgagacc | ataccaattt | ttcggaaatg | actcaggtcc | tgatcgaccg | gaacaatttc | 1020 |
| gtcgggctgt | acccgcagga | tggagagcat | cccgacgcga | ttcagttcat | gaccgctggc | 1080 |
| cgcgccaagg | caaataccgg | gatcaccatc | tcgaataacg | tcatcatgca | agggatggg | 1140 |
| ctgggcaccc | aaggggtctt | cctgggcgag | gagaccggca | accttcccta | caaggacgtg | 1200 |
| actatcaaca | caatctgat | ctatctcagc | ggcctgtatc | atggcatcaa | cgtcgtgaac | 1260 |
| ggcagcaatg | taaatatcac | caacaacagc | acgctgtctg | tggccgatga | acgatcgacc | 1320 |
| tggattcgtg | tcgaaaacgt | gacgagcggg | tcaatcgtca | ataacgtcgc | ggatgagatc | 1380 |
| attgcagcga | acagtgcagg | tgtcacgctt | tccaagaatg | tcagcctagt | caaggactcg | 1440 |
| gtcgcgcttc | gcaagatccc | ggacctacac | ctcggagcgg | cggcgcgcgt | ggccgggctc | 1500 |
| gtcctgcctg | gcgtgggcta | taatcctggc | accagcagtt | ccgggaccgc | gtcgacccct | 1560 |
| cagccgccca | agctgctgct | tgacctcaac | ttcgcgtcga | caggtgcaat | tgattcgtcg | 1620 |
| atctggagct | cggacgaaac | agtctccccc | cttgccgccg | gggccgtaag | cgatggcatg | 1680 |
| gtgcgcgtcc | agaccggctc | tggtgtcgaa | ctgggggcgtg | acacgtcgcg | gcagctattt | 1740 |
| agcctatcgg | ctttcactct | gaacttcaat | ctgaagcgcg | acgcacccaa | tgcggcggtc | 1800 |
| ggccagatca | tgggcgtctt | caagagctgg | gcgatcaatc | tggggcgaa | cggtgaactg | 1860 |
| accttcacga | tgaccaatgc | cgcgggcaag | acctcgaccc | ttacaaccaa | ggggccaag | 1920 |
| atcaccgacg | cgaacctgca | taggatcgcc | cttacctatg | acagtgcacg | tggaacggcc | 1980 |

-continued

```
gcgatctatg tcgacggcgt ggtgcggggc acggcggcga tgtccggcag tacgcgcgct    2040
caagagttct ggggcgtgta tctcggcggc cagttcacga acgctttcag cggctcgctt    2100
ggtgacatcg aggttcgaga cgccgcattg agtgcggcgc aaatcgtcgc tctaaatgcc    2160
aacagcagcg tgaccgccac aggggtgcag gcggcggacg ctgtgagggc gacggtggta    2220 aatgggcgg cgagcaccgc ggcggcgtta atgagcggga cgactgtcga cggggccacc    2280
acctcgctgc cgacgttgac gctgctcggc gggtcggtcg gtgccggtag cgtgcaatcc    2340
ccgctcgcaa gcgctatcgc aaaagccgtc aacgcgcaga cgactggctc gctttccaag    2400
ccgacaagct ttctttcagg ttcttggatg cagatgctcg atgcgttcca cgcctgacgg    2460
gcgcgccggt tgccgcgctt gctcaggcta gtgccatggc ctaagcgagc ggtgctatcg    2520
ttgggggggc tgggtgaaga gagaagtatt gcatctgcgc ggcgtgcgcg ccagatggt    2580 ggttggcttc ggggttaagg gtctcggcgc cgttaccagc tttctcttca cctggcttct    2640
ggcccgtgcc gccggtcctg tgggcgttgg cacgttcggt acgtcgttga cgacggtcca    2700
gatgtgcgtg atcttgtcgt tgctaggcct cgatgcgatc ctcgtgcgct cggtgtcggt    2760
gaatctgtcg ctgaaacgca ctgggcaggc aaggtcggct gccgtgcacg caattcggat    2820
gggagcggcg gcgggtctca ccctgatgag cgcgatcg                            2858
```

<210> SEQ ID NO 28
<211> LENGTH: 659
<212> TYPE: PRT
<213> ORGANISM: Sphingomonas elodea

<400> SEQUENCE: 28

```
Met Pro Ala Ile Thr Val Lys Asn Gln Ala Glu Leu Asp Ala Ile
1               5                   10                  15

Lys Thr Ala Lys Gly Gly Asp Thr Ile Leu Ala Pro Gly Thr Tyr
                20                  25                  30

Ser Ser Val Thr Met Thr Asn Ile Lys Pro Ala Thr Val Leu Thr Ile
                35                  40                  45

Gln Ser Leu Asp Thr Lys Asn Pro Ala Val Val Gln Ser Leu Trp Ile
    50                  55                  60

Ser Ser Asn Asn Ile Thr Phe Lys Asp Leu Asp Val Lys Arg Asp
65                  70                  75                  80

Tyr Arg Pro Ala Asn Asp Trp Glu Thr Ala Ser Arg Ile Leu Asn Ser
                85                  90                  95

Asn Asn Ile Thr Val Asp Asn Val Arg Phe Ser Gly Gly Ser Gly Asp
                100                 105                 110

Pro Ala Leu Ser Thr Gly Val Gly Leu Ser Ile Arg Ser Gly Thr Asn
            115                 120                 125

Ile Lys Phe Leu Asn Ser Ser Val Asp His Phe Gly Leu Gly Leu Ser
    130                 135                 140

Val Gln Asp Ile Asn Lys Met Thr Val Gln Gly Ser Thr Phe Arg Asp
145                 150                 155                 160

Asn Arg Arg Asp His Thr Asn Phe Ser Glu Met Thr Gln Val Leu Ile
                165                 170                 175

Asp Arg Asn Asn Phe Val Gly Leu Tyr Pro Gln Asp Gly Glu His Pro
                180                 185                 190

Asp Ala Ile Gln Phe Met Thr Ala Gly Arg Ala Lys Ala Asn Thr Gly
            195                 200                 205

Ile Thr Ile Ser Asn Asn Val Ile Met Gln Gly Asp Gly Leu Gly Thr
    210                 215                 220
```

-continued

```
Gln Gly Val Phe Leu Gly Glu Thr Gly Asn Leu Pro Tyr Lys Asp
225                 230                 235                 240

Val Thr Ile Asn Asn Asn Leu Ile Tyr Leu Ser Gly Leu Tyr His Gly
        245                 250                 255

Ile Asn Val Val Asn Gly Ser Asn Val Asn Ile Thr Asn Asn Ser Thr
            260                 265                 270

Leu Ser Val Ala Asp Glu Arg Ser Thr Trp Ile Arg Val Glu Asn Val
        275                 280                 285

Thr Ser Gly Ser Ile Val Asn Asn Val Ala Asp Glu Ile Ile Ala Ala
    290                 295                 300

Asn Ser Ala Gly Val Thr Leu Ser Lys Asn Val Ser Leu Val Lys Asp
305                 310                 315                 320

Ser Val Ala Leu Arg Lys Ile Pro Asp Leu His Leu Gly Ala Ala Ala
                325                 330                 335

Arg Val Ala Gly Leu Val Leu Pro Gly Val Gly Tyr Asn Pro Gly Thr
            340                 345                 350

Ser Ser Ser Gly Thr Ala Ser Thr Leu Gln Pro Pro Lys Leu Leu Leu
        355                 360                 365

Asp Leu Asn Phe Ala Ser Thr Gly Ala Ile Asp Ser Ser Ile Trp Ser
    370                 375                 380

Ser Asp Glu Thr Val Ser Pro Leu Ala Ala Gly Ala Val Ser Asp Gly
385                 390                 395                 400

Met Val Arg Val Gln Thr Gly Ser Gly Val Glu Leu Gly Arg Asp Thr
                405                 410                 415

Ser Arg Gln Leu Phe Ser Leu Ser Ala Phe Thr Leu Asn Phe Asn Leu
            420                 425                 430

Lys Arg Asp Ala Pro Asn Ala Ala Val Gly Gln Ile Met Gly Val Phe
        435                 440                 445

Lys Ser Trp Ala Ile Asn Leu Gly Ala Asn Gly Glu Leu Thr Phe Thr
    450                 455                 460

Met Thr Asn Ala Ala Gly Lys Thr Ser Thr Leu Thr Thr Lys Gly Ala
465                 470                 475                 480

Lys Ile Thr Asp Ala Asn Leu His Arg Ile Ala Leu Thr Tyr Asp Ser
                485                 490                 495

Ala Arg Gly Thr Ala Ala Ile Tyr Val Asp Gly Val Val Arg Gly Thr
            500                 505                 510

Ala Ala Met Ser Gly Ser Thr Arg Ala Gln Glu Phe Trp Gly Val Tyr
        515                 520                 525

Leu Gly Gly Gln Phe Thr Asn Ala Phe Ser Gly Ser Leu Gly Asp Ile
    530                 535                 540

Glu Val Arg Asp Ala Ala Leu Ser Ala Ala Gln Ile Val Ala Leu Asn
545                 550                 555                 560

Ala Asn Ser Ser Val Thr Ala Thr Gly Val Gln Ala Ala Asp Ala Val
                565                 570                 575

Arg Ala Thr Val Val Asn Gly Ala Ala Ser Thr Ala Ala Leu Met
            580                 585                 590

Ser Gly Thr Thr Val Asp Gly Ala Thr Thr Ser Leu Pro Thr Leu Thr
        595                 600                 605

Leu Leu Gly Gly Ser Val Gly Ala Gly Ser Val Gln Ser Pro Leu Ala
    610                 615                 620

Ser Ala Ile Ala Lys Ala Val Asn Ala Gln Thr Thr Gly Ser Leu Ser
625                 630                 635                 640

Lys Pro Thr Ser Phe Leu Ser Gly Ser Trp Met Gln Met Leu Asp Ala
```

Phe His Ala

<210> SEQ ID NO 29
<211> LENGTH: 1972
<212> TYPE: DNA
<213> ORGANISM: Sphingomonas sp.
<220> FEATURE:
<221> NAME/KEY: gene
<222> LOCATION: (501)..(1472)

<400> SEQUENCE: 29

```
ctggacgatc gtcaccgtcg cgatgccctt caccatcttg ccgaaggcag acgggtggtc        60
gaagcgcgcg aagctttcga tatggacgaa cttggcgccc gacagtttgg cgagcagcgc       120
ggtgaaatag actgcgcccg cgccggtgga aataccacca tccggcttgt gccggcgcag       180
gatcgaaagg ctctggcgca ggttgcgcca tgcgccgccc agcatgcgca agggatggcc       240
cagcttggcc tggccgagcg catagtgctc caccagttcg acgggatgtt tttcggcaag       300
gctccggccg agcgcggtat cttcagtaac gaagaaataa tcgtgttcgc gccacaccga       360
ttccagatcg aggatttgcc ggagatggcc gccgcccgac gctgcaaggc acattttcag       420
cggcttggag gcctttccat ctaccgcgtt cgcttctgcc atctcgtccc ccttgttgcc       480
gcctggctcc gcttagaacc atgctgcact gccaacgcta ttgcggatgc cgcccgtcc        540
gaataggttc aagtagaagt ttgtgccgtg cgcaattccg tgccggcggg gaggtcttca       600
tgaagaaatt gtacctggtt acggcggtgg ctgcggccgc gctggccgtc tccggatgtg       660
gcggcaaggg cggcaagctc gacaagggc aggtggtcgc cagcgtcgat ggcgaagaaa        720
tcaccgtctt cgagctgaat gccgaactgc aggcctccca ggtaccccg gggaccgatc        780
gcaagctggc cgagcagctg gcgctgcagc gcatcatcga gcgcaagatc ctcgccaagg       840
tcgcccgcga gcagaagctg acaagacgcg ctgccttcct gatccaggag cgccgggccg       900
acgagctgat cctcaccgcc atgctgcgcg acaagatcgc cggcggcatc gcccagccga       960
ccgatgccga gatcgagaaa tatcaggccg cgcatccgga gcggttcgcg cagcgcaaga      1020
tctacgcgat cgatcaggtc gtcttcgctc cgccgagctc ggccgcaaag ctcaagcaat      1080
tcgcgccgct gaagacgctg gaccagctaa ccgccaagct ctcggcggac aatgtccagt      1140
tccgtcgcgc gccgtcgcag atcgacaccg ctgcgctgcc gccggaaatc gctgccaaga      1200
tcgcgtcgct gccggcacag gagatgttca tcctgccgac ccagcaggga ctgaccgcga      1260
atatcatcac gtcgaccacg gtgctgccgg tgccggccga ccaggcgcgc gagatcgcgc      1320
tcagcgggct gcgtaccgag cgcttcggca aggcggctga cgcacagctc aacgaccgcc      1380
tgaagaaggc gcgggaaacc gtgaaatatc aggccggcta cagcgcaccg ccgcagcttc      1440
gcggcagcgg cgcaacgccg gcggggaact gaaggtctga aaggcgggcg cgttgttgca      1500
acgatgcgtc cgcctcccaa cggcgccttt agggggggg gagctggact tttagcgacg       1560
cggatagccg ctccaccatc ggccaggatt gctaaatacg gcacgccacc cgttgctcag      1620
ctctttgtat cgcgtgcccg tccgcggcga caggcgccag agtgccgccc cgaccaacgt      1680
gtatttggcg gcgatcagcc aaagcgcgca cccggtggca agggtgccga gtgcgccaaa      1740
atgctttcgc gcatagtgca tgcgcccggt cgtgagatac atcaggcggt tctgggacat      1800
cgactgacca ctccccgtat tgtgtaccac tttgaccgag gggtcgacga gcaccttgtg      1860
ccccaacgtg cggattcgct ggaagagatc gatctcttcc gaataaagaa aaaagctctc      1920
gtcaaaaccg ccgatcgcct gccagacatc ggtgcgtacc atcatgaagc cg             1972
```

<210> SEQ ID NO 30
<211> LENGTH: 323
<212> TYPE: PRT
<213> ORGANISM: Sphingomonas sp.

<400> SEQUENCE: 30

Met Leu His Cys Gln Arg Tyr Cys Gly Cys Pro Val Arg Ile Gly
1               5                   10                  15

Ser Ser Arg Ser Leu Cys Arg Ala Gln Phe Arg Ala Gly Gly Glu Val
            20                  25                  30

Phe Met Lys Lys Leu Tyr Leu Val Thr Ala Val Ala Ala Ala Leu
            35                  40                  45

Ala Val Ser Gly Cys Gly Gly Lys Gly Gly Lys Leu Asp Lys Gly Gln
    50                  55                  60

Val Val Ala Ser Val Asp Gly Glu Glu Ile Thr Val Phe Glu Leu Asn
65                  70                  75                  80

Ala Glu Leu Gln Ala Ser Gln Val Pro Pro Gly Thr Asp Arg Lys Leu
                85                  90                  95

Ala Glu Gln Leu Ala Leu Gln Arg Ile Ile Glu Arg Lys Ile Leu Ala
            100                 105                 110

Lys Val Ala Arg Glu Gln Lys Leu Asp Lys Thr Pro Ala Phe Leu Ile
            115                 120                 125

Gln Glu Arg Arg Ala Asp Glu Leu Ile Leu Thr Ala Met Leu Arg Asp
        130                 135                 140

Lys Ile Ala Gly Gly Ile Ala Gln Pro Thr Asp Ala Glu Ile Glu Lys
145                 150                 155                 160

Tyr Gln Ala Ala His Pro Glu Arg Phe Ala Gln Arg Lys Ile Tyr Ala
                165                 170                 175

Ile Asp Gln Val Val Phe Ala Pro Pro Ser Ser Ala Ala Lys Leu Lys
            180                 185                 190

Gln Phe Ala Pro Leu Lys Thr Leu Asp Gln Leu Thr Ala Lys Leu Ser
        195                 200                 205

Ala Asp Asn Val Gln Phe Arg Arg Ala Pro Ser Gln Ile Asp Thr Ala
    210                 215                 220

Ala Leu Pro Pro Glu Ile Ala Ala Lys Ile Ala Ser Leu Pro Ala Gln
225                 230                 235                 240

Glu Met Phe Ile Leu Pro Thr Gln Gln Gly Leu Thr Ala Asn Ile Ile
                245                 250                 255

Thr Ser Thr Thr Val Leu Pro Val Pro Ala Asp Gln Ala Arg Glu Ile
            260                 265                 270

Ala Leu Ser Gly Leu Arg Thr Glu Arg Phe Gly Lys Ala Ala Asp Ala
        275                 280                 285

Gln Leu Asn Asp Arg Leu Lys Lys Ala Arg Glu Thr Val Lys Tyr Gln
    290                 295                 300

Ala Gly Tyr Ser Ala Pro Pro Gln Leu Arg Gly Ser Gly Ala Thr Pro
305                 310                 315                 320

Ala Gly Asn

<210> SEQ ID NO 31
<211> LENGTH: 2998
<212> TYPE: DNA
<213> ORGANISM: Sphingomonas sp.
<220> FEATURE:
<221> NAME/KEY: gene
<222> LOCATION: (501)..(2498)

<400> SEQUENCE: 31

```
tgcgccgggc tggggaatgg catcggggtt gacgagcagc aggagcgggc cggcagcctg        60
cgctgccagg cgattattgc cggccccgaa accaatattg ccctcactgg gaacgatgcg       120
gacgtggtgg aaccgctgcc ggaccagcgc ttcggttcgc ccgtcgccat tgtcgatcag       180
cagaacttcg tgggggtct tgcccgctcc ttcggcgatg ccgcgcaggc agtcttcgat        240
atactcggtc gagttgaaag cgaccacgag tatgctgaca tcgggcgttg ggagcatctg       300
catcgcaccc tagtagctgc actgtgttgc gccgtcgaga cggtgccggc gaaagtcggg       360
cgtgcatggg cccggcatgc ggccccgtag aagggagttc ttaactgtat cccttcgagc       420
aaatttcatg gctgttctgg tatttatgac aatggaaggg tcaatatcgg cccgggttcg       480
tgcgtacggg gtaagtcaac atgccggata tcattgtcaa gaatcagacg gagttgaatg       540
ctgcaatcgc ggcggcgaag ggtggcgaaa ccatcaagct tgccgccggg gtctacacag       600
atctcactgt aatgaccaag acgtttacca gcatggtgac aattgagtcg ctcgactcgt       660
cgaacccggt caatatccaa aagctggtga tcgggaacag tagcaacgtt accgtcaaaa       720
acatggtcgc tgcgaccgat tacaagcccg ccgatgactg gaatcgactg aatacgatcc       780
agggttcggc caacatcgtt ttggacggcg tgcggttcag cggcggcact ggtgacccctt      840
cgctctcgaa gggggcgggc ttgttcgtgc gcaacagcac gtcggtgacg atgcagaatt       900
cgtctatcga ccacttcggt ctgggccttg aggcctacaa cgtcgatggc atggtggtcc       960
agaacagcag cttccacgac aaccggcgcg atcatacgaa cttcactgag atgaacaatc      1020
ttgtcatcga cggaaattcg ttcacgaacc tgtttcccgt gggcaccgaa catcccgacg      1080
ccattcagtt cttcacggcg ggcaaggtca agggcaatac caacatcacc atctccaata      1140
acgtcatcat gcagggcgcg ggctctggcg cgcaagggat tttcatgaat gacgaggccg      1200
gtaatcttcc ctatgtcaat gtaaacatca aaaacaatct tatctatctg aatggttatt      1260
accacggtat caacgttgtt aacggcgtta atgtcaatat cgaatccaat agcgtgatat      1320
cgcaagtgga tggcacatca ttttggattc gcctcgacaa aaccaatggc gcgacgatca      1380
agaacaatgt tgcggacctg atcaccgtca caagctcctc gagcaatatc gtgcagacag      1440
gcaatcgtac gctgacgagt gactcggcaa cgatccgcaa gatctatggc ctcaacgatg      1500
gggctacggc gcggctcagc gatttgatcg ttcccggcgt cgggtaccag ccgcccgtgt      1560
cgagcgctgc tgccgctcag gtgactaccg aactgtcgac tgcgaaggcg caaatccgt       1620
cgctgctgct cgatctgtcg ttcagcaaca gcggcgtcgt ggaccttccg cactggaata      1680
ccggccagac gacaaaggcg gtggacgtgt cggcggtcgt gggcagcgcc ttccacgtct      1740
cgacgggcac ggggtggaa ctaaaccgga gctattcgcg gcagatttac gcattgtcgg       1800
cgttcacgct cagcttcgac ctcaagcggg actcggctac ggccacggcc gggcaaattc      1860
ttggcatctt ccagagctgg tcggtttcgc tgcaggccaa tggggaactg agcttcacca      1920
tgcgcaacgc cgcgggcgtc agccagacaa tggtgacgag cggcgccaag ctgcttgatg      1980
ctgccacaca caagatcgcc ctgacctacg acagcacgcg gaaaaccgcg attctgtacg      2040
tagacggcat gcaacgcggc acagcgacga tgaccggcac gacccggccc gccgaatcct      2100
ggggggctgta tgtcggcagc ccgttctcga ccgcattcag cggaacggtc ggcgacatcg      2160
agatccgcga tggcgcgatc agcgccgccc aggtgcaggc gctggtgacc gcgtcgagcg      2220
ccagcgcggc ggcgacggtc aaggacagcc tcgtcaccgg cgcggccgcg caggccgctg      2280
cgctgctggc gggtgccggc gccgctagca cggcaacgcc gcttgcgacg gtggccacgg      2340
```

```
tgggcagtac gctgtctata ggtactgccg cgtcctcgca gatcgcgctc gtcagcaaga    2400
tcggtgtcga catgatgacc gcgggggcga tgggcgcaat ccgcagcgcg gcgacactga    2460
gcgctacggc ggatcagtac aacctgtacc gcgcctgagc gggggcgggc ggtgagcggc    2520
cttgcgccgg cgccgcccgt gccctcctgc gatccggcgg cacatcgcag ggagtgcggc    2580
gtatcgacct tgcttttcgc gaaccccttcg atcatgcgag cggcagcgcc tcttggggac    2640
ttgttgggga cttgcagatg acgactacct cggcgtttcg tcgcccggcc ttccacggag    2700
cgatgcagcg gcttcgcagg ttgcgactgg ttcggtttct gacaaagcca gcgatcccgg    2760
tactgcccgt ctacaaagcc gagcgatcag gcgtgacgat cgcggcgcgg cgtaccgttc    2820
tgctggtcag cgtgatgttt cttgccgcag tctacggcct gctcgccgca gttctgccgc    2880
tccagatgct ggcgatcccg gccgtgcccc tcgttctgat ggcgctcgta gtgatctggg    2940
cgctacccga ggcgcggcag gcgcctactc gcctgctggc aaaactatac ctcgccta     2998
```

```
<210> SEQ ID NO 32
<211> LENGTH: 665
<212> TYPE: PRT
<213> ORGANISM: Sphingomonas sp.

<400> SEQUENCE: 32

Met Pro Asp Ile Ile Val Lys Asn Gln Thr Glu Leu Asn Ala Ala Ile
1               5                   10                  15

Ala Ala Ala Lys Gly Gly Glu Thr Ile Lys Leu Ala Ala Gly Val Tyr
            20                  25                  30

Thr Asp Leu Thr Val Met Thr Lys Thr Phe Thr Ser Met Val Thr Ile
        35                  40                  45

Glu Ser Leu Asp Ser Ser Asn Pro Val Asn Ile Gln Lys Leu Val Ile
    50                  55                  60

Gly Asn Ser Ser Asn Val Thr Val Lys Asn Met Val Ala Ala Thr Asp
65                  70                  75                  80

Tyr Lys Pro Ala Asp Asp Trp Asn Arg Leu Asn Thr Ile Gln Gly Ser
                85                  90                  95

Ala Asn Ile Val Leu Asp Gly Val Arg Phe Ser Gly Gly Thr Gly Asp
            100                 105                 110

Pro Ser Leu Ser Lys Gly Ala Gly Leu Phe Val Arg Asn Ser Thr Ser
        115                 120                 125

Val Thr Met Gln Asn Ser Ser Ile Asp His Phe Gly Leu Gly Leu Glu
    130                 135                 140

Ala Tyr Asn Val Asp Gly Met Val Val Gln Asn Ser Ser Phe His Asp
145                 150                 155                 160

Asn Arg Arg Asp His Thr Asn Phe Thr Glu Met Asn Asn Leu Val Ile
                165                 170                 175

Asp Gly Asn Ser Phe Thr Asn Leu Phe Pro Val Gly Thr Glu His Pro
            180                 185                 190

Asp Ala Ile Gln Phe Phe Thr Ala Gly Lys Val Lys Gly Asn Thr Asn
        195                 200                 205

Ile Thr Ile Ser Asn Asn Val Ile Met Gln Gly Ala Gly Ser Gly Ala
    210                 215                 220

Gln Gly Ile Phe Met Asn Asp Glu Ala Gly Asn Leu Pro Tyr Val Asn
225                 230                 235                 240

Val Asn Ile Lys Asn Asn Leu Ile Tyr Leu Asn Gly Tyr Tyr His Gly
                245                 250                 255

Ile Asn Val Val Asn Gly Val Asn Val Asn Ile Glu Ser Asn Ser Val
            260                 265                 270
```

```
Ile Ser Gln Val Asp Gly Thr Ser Phe Trp Ile Arg Leu Asp Lys Thr
            275                 280                 285

Asn Gly Ala Thr Ile Lys Asn Asn Val Ala Asp Leu Ile Thr Val Thr
        290                 295                 300

Ser Ser Ser Ser Asn Ile Val Gln Thr Gly Asn Arg Thr Leu Thr Ser
305                 310                 315                 320

Asp Ser Ala Thr Ile Arg Lys Ile Tyr Gly Leu Asn Asp Gly Ala Thr
                325                 330                 335

Ala Arg Leu Ser Asp Leu Ile Val Pro Gly Val Gly Tyr Gln Pro Pro
            340                 345                 350

Val Ser Ser Ala Ala Ala Gln Val Thr Thr Glu Leu Ser Thr Ala
        355                 360                 365

Lys Ala Ala Asn Pro Ser Leu Leu Leu Asp Leu Ser Phe Ser Asn Ser
370                 375                 380

Gly Val Val Asp Leu Ser His Trp Asn Thr Gly Gln Thr Thr Lys Ala
385                 390                 395                 400

Val Asp Val Ser Ala Val Val Gly Ser Ala Phe His Val Ser Thr Gly
                405                 410                 415

Thr Gly Val Glu Leu Asn Arg Ser Tyr Ser Arg Gln Ile Tyr Ala Leu
            420                 425                 430

Ser Ala Phe Thr Leu Ser Phe Asp Leu Lys Arg Asp Ser Ala Thr Ala
        435                 440                 445

Thr Ala Gly Gln Ile Leu Gly Ile Phe Gln Ser Trp Ser Val Ser Leu
    450                 455                 460

Gln Ala Asn Gly Glu Leu Ser Phe Thr Met Arg Asn Ala Ala Gly Val
465                 470                 475                 480

Ser Gln Thr Met Val Thr Ser Gly Ala Lys Leu Leu Asp Ala Ala Thr
                485                 490                 495

His Lys Ile Ala Leu Thr Tyr Asp Ser Thr Arg Lys Thr Ala Ile Leu
            500                 505                 510

Tyr Val Asp Gly Met Gln Arg Gly Thr Ala Thr Met Thr Gly Thr Thr
        515                 520                 525

Arg Pro Ala Glu Ser Trp Gly Leu Tyr Val Gly Ser Pro Phe Ser Thr
530                 535                 540

Ala Phe Ser Gly Thr Val Gly Asp Ile Glu Ile Arg Asp Gly Ala Ile
545                 550                 555                 560

Ser Ala Ala Gln Val Gln Ala Leu Val Thr Ala Ser Ala Ser Ala
                565                 570                 575

Ala Ala Thr Val Lys Asp Ser Leu Val Thr Gly Ala Ala Gln Ala
            580                 585                 590

Ala Ala Leu Leu Ala Gly Ala Gly Ala Ala Ser Thr Ala Thr Pro Leu
        595                 600                 605

Ala Thr Val Ala Thr Val Gly Ser Thr Leu Ser Ile Gly Thr Ala Ala
    610                 615                 620

Ser Ser Gln Ile Ala Leu Val Ser Lys Ile Gly Val Asp Met Met Thr
625                 630                 635                 640

Ala Gly Ala Met Gly Ala Ile Arg Ser Ala Thr Leu Ser Ala Thr
                645                 650                 655

Ala Asp Gln Tyr Asn Leu Tyr Arg Ala
            660                 665
```